(12) United States Patent
Kitagawa et al.

(10) Patent No.: US 9,194,866 B2
(45) Date of Patent: Nov. 24, 2015

(54) SAMPLE ANALYZER

(71) Applicant: Sysmex Corporation, Kobe-shi Hyogo (JP)

(72) Inventors: Nobuhiro Kitagawa, Kobe (JP); Yuichi Hamada, Kobe (JP); Takaaki Nagai, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 14/030,638

(22) Filed: Sep. 18, 2013

(65) Prior Publication Data

US 2014/0050622 A1  Feb. 20, 2014

Related U.S. Application Data

(63) Continuation of application No. PCT/JP2012/001994, filed on Mar. 22, 2012.

(30) Foreign Application Priority Data

Mar. 23, 2011  (JP) ................... 2011-063956

(51) Int. Cl.
*G01N 33/50* (2006.01)
*G01N 35/10* (2006.01)
*G01N 35/00* (2006.01)
*G01N 35/02* (2006.01)

(52) U.S. Cl.
CPC ...... *G01N 33/5094* (2013.01); *G01N 35/00732* (2013.01); *G01N 35/026* (2013.01); *G01N 2035/00782* (2013.01); *G01N 2035/00792* (2013.01)

(58) Field of Classification Search
CPC .............. G01N 35/00732; G01N 2035/00782; G01N 2035/00792
See application file for complete search history.

(56) References Cited

U.S. PATENT DOCUMENTS

| 5,171,538 | A | * | 12/1992 | Tremmel et al. ............. 422/509 |
| 2003/0070498 | A1 | | 4/2003 | Ohyama et al. |
| 2004/0105784 | A1 | * | 6/2004 | Fukuju et al. ............... 422/68.1 |
| 2004/0207564 | A1 | | 10/2004 | Kawakami et al. |

(Continued)

FOREIGN PATENT DOCUMENTS

| DE | 102007012524 A1 | * | 9/2008 |
| JP | 2002-055110 A | | 2/2002 |
| JP | 2003-075458 A | | 3/2003 |

(Continued)

OTHER PUBLICATIONS

International Search Report for International Application No. PCT/JP2012/001994, dated May 1, 2012, 2 pages.

*Primary Examiner* — P. Kathryn Wright
(74) *Attorney, Agent, or Firm* — Brinks Gilson & Lione

(57) ABSTRACT

Each of a first measurement unit and a second measurement unit (sample analyzer) includes: a reagent storage section in which a plurality of holder parts are arranged side by side, each of the holder parts including a setting part in which a reagent container having an RFID tag attached thereto is set, and an antenna part which transmits/receives a radio wave to/from the RFID tag of the reagent container set in the setting part; and a left face part and a right face part which block a radio wave communication path between the antenna part of one of the holder parts and the RFID tag of the reagent container set in another one, of the holder parts, adjacent to the one of the holder parts.

19 Claims, 13 Drawing Sheets

(56) References Cited

U.S. PATENT DOCUMENTS

2008/0024301 A1    1/2008   Fritchie et al.
2010/0132484 A1    6/2010   Schacher et al.

FOREIGN PATENT DOCUMENTS

| | | |
|---|---|---|
| JP | 2004-106542 A | 4/2004 |
| JP | 2004-163319 A | 6/2004 |
| JP | 2004-271299 A | 9/2004 |
| JP | 2005125144 A * | 5/2005 |
| JP | 2009-210444 A | 9/2009 |
| JP | 2009-544972 A | 12/2009 |
| JP | 2010-127936 A | 6/2010 |
| WO | WO 2008/014117 A2 | 1/2008 |

* cited by examiner

SAMPLE ANALYZER

RELATED APPLICATIONS

This application is a continuation of PCT/JP2012/001994 filed on Mar. 22, 2012, which claims priority to Japanese Application No. 2011-063956 filed on Mar. 23, 2011. The entire contents of these applications are incorporated herein by reference.

BACKGROUND OF THE INVENTION

1. Field of the Invention

The present invention relates to sample analyzers, and in particular, to sample analyzers that analyze samples using reagents contained in reagent containers.

2. Description of the Background Art

To date, there are known sample analyzers that analyze samples using reagents contained in reagent containers (for example, see Japanese Laid-Open Patent Publication 2009-210444).

Japanese Laid-Open Patent Publication 2009-210444 discloses an automatic analyzer that includes a cylindrical reagent container holding part in which reagent containers each having a radio IC tag (storage medium) attached thereto are concentrically arranged in two circles. The innermost periphery (inner peripheral wall) in this reagent container holding part is provided with one inner antenna part that corresponds to the circle of the reagent containers on the inner peripheral side. Further, the outermost periphery (outer peripheral wall) in the reagent container holding part is provided with one outer antenna part that corresponds to the circle of the reagent containers on the outer peripheral side. That is, in the reagent container holding part, along a radial direction, the inner antenna part, a reagent container on the inner peripheral side, a reagent container on the outer peripheral side, and the outer antenna part are arranged in this order. This automatic analyzer is configured to perform reading and writing of information of the radio IC tag of each reagent container on the inner peripheral side by use of the inner antenna part, and to perform reading and writing of information of the radio IC tag of each reagent container on the outer peripheral side by use of the outer antenna part. Accordingly, it is possible to manage reagent information of the reagents (reagent containers) set on the reagent container holding part.

In general, a radio wave emitted from an antenna part spreads not only to the vicinity of the antenna part but also to the surrounding area of the antenna part. Thus, in a configuration as in Japanese Laid-Open Patent Publication No. 2009-210444 where a plurality of reagent containers and a plurality of antenna parts corresponding to the reagent containers are provided, and a corresponding antenna part performs wireless communication with the radio IC tag of a particular reagent container, a radio wave emitted from a first antenna part may reach not only the radio IC tag of a first reagent container being a target but also the radio IC tag of a second reagent container not being a target, and similarly, a radio wave emitted from a second antenna part may reach not only the radio IC tag of the second reagent container being a target but also the radio IC tag of the first reagent container not being a target. Therefore, there is a risk of occurrence of erroneous reading/writing of information.

SUMMARY OF THE INVENTION

The present invention has been made in order to solve the above problem. An object of the present invention is to provide a sample analyzer that can prevent occurrence of erroneous reading/writing of information from/to a storage medium of a reagent container other than a target reagent container.

In order to achieve the above object, a sample analyzer in one aspect of the present invention is a sample analyzer which analyzes a sample using a reagent contained in a reagent container, the sample analyzer including: a reagent storage section in which a plurality of reagent holder parts are arranged, each of the reagent holder parts including a setting part in which a reagent container having a storage medium attached thereto is set, and a radio wave communication part which transmits and receives a radio wave to and from the storage medium of the reagent container set in the setting part; and a radio wave blocking part which blocks a radio wave communication path between the radio wave communication part of one of the reagent holder parts and the storage medium of the reagent container set in another reagent holder part that is adjacent to the one of the reagent holder parts. It should be noted that the "radio wave blocking part" in the present invention represents a wide concept including not only those that completely block radio waves but also those attenuate radio waves to an extent that does not allow communication.

In the sample analyzer according to the above aspect of the present invention, as described above, the radio wave blocking part is provided which blocks the radio wave communication path between the radio wave communication part of one of the reagent holder parts and the storage medium of the reagent container set in another reagent holder part that is adjacent to the one of the reagent holder parts. Accordingly, of the radio wave emitted from the radio wave communication part of the one of the reagent holder parts, the radio wave advancing to the storage medium of the reagent container set in said adjacent another reagent holder part can be blocked by the radio wave blocking part. As a result, in each reagent holder part, it is possible to read and write information from and to the storage medium of the reagent container set in its own setting part, and at the same time, it is possible to prevent occurrence of reading and writing information from and to the storage medium of the reagent container in said adjacent another reagent holder part. Accordingly, it is possible to prevent occurrence of erroneous reading and writing of information from and to the storage mediums of the reagent containers other than the target reagent container.

In the sample analyzer according to the above aspect, preferably, the radio wave blocking part is provided so as to be located, when a reagent container is set in the setting part of said another reagent holder part, between the radio wave communication part of the one of the reagent holder parts and the storage medium of the reagent container set in the setting part of said another reagent holder part. In this configuration, it is possible to assuredly block the radio wave communication path between the radio wave communication part of the one reagent holder part and the storage medium of the reagent container set in said another reagent holder part adjacent to the one reagent holder part.

In the sample analyzer according to the above aspect, preferably, each of the reagent holder parts is formed from a conductive material having a shape surrounding the reagent container set in the setting part thereof, and the conductive material forms the radio wave blocking part. In this configuration, it is possible to more assuredly prevent occurrence of reading and writing of information from and to the storage mediums of non-target reagent containers set in other reagent holder parts, by the radio wave blocking part formed from the conductive material having a shape surrounding the reagent container set in the setting part.

In this case, preferably, in the conductive material, a cutout is formed at a position corresponding to the radio wave communication part. In this configuration, it is possible to assuredly perform reading and writing of information to the storage medium of the target reagent container, through the cutout formed in the conductive material (radio wave blocking part). Meanwhile, in a case where a window-like opening part is formed in the conductive material (radio wave blocking part), for example, a loop portion around the opening part may serve as if it were an antenna due to electromagnetic induction or the like. As a result, communication between the radio wave communication part and the storage medium may be disturbed. In the present invention, by forming a cutout at a position corresponding to the radio wave communication part, formation of the conductive body loop around the cutout (radio wave blocking part) can be prevented. Therefore, communication can be performed in a good condition between the radio wave communication part and the storage medium via the cutout.

In the configuration in which the cutout is formed in the conductive material, preferably, the cutout has a shape not forming a loop.

In the configuration in which the cutout is formed in the conductive material, preferably, the sample analyzer further includes a protection member provided so as to cover the cutout and formed from a radio wave transmissive material that allows a radio wave to pass therethrough, and the radio wave communication part is attached to the protection member. In this configuration, the space between the radio wave communication part and the reagent container set in the setting part can be separated by the protection member provided so as to cover the cutout. Accordingly, it is possible to prevent liquid drops of the reagent contained in the reagent container from attaching to the radio wave communication part, and to prevent the reagent container from being brought into contact with the radio wave communication part when the reagent container is to be set. Further, since the protection member can also be used as an attachment member for the radio wave communication part, the number of components can be reduced compared with a case where the radio wave communication part and the protection member are separately attached to the reagent holder part.

In the sample analyzer according to the above aspect, preferably, the plurality of reagent holder parts are arranged in a line along a predetermined direction, and each of the reagent holder parts includes the radio wave communication part thereof, the setting part thereof, and the radio wave blocking part thereof along the predetermined direction in this order. In this configuration, in each of the plurality of reagent holder parts arranged along the predetermined direction, a radio wave blocking part is always arranged between the radio wave communication part of one of two adjacent reagent holder parts and the setting part of the other of the two adjacent reagent holder parts. Accordingly, also in a case where a plurality of reagent holder parts are arranged close to each other along the predetermined direction, it is possible to assuredly perform reading and writing of information from and to the storage medium of the target reagent container, while blocking the communication paths to the storage mediums of the reagent containers set in the setting parts of other reagent holder parts.

In the sample analyzer according to the above aspect, preferably, each reagent holder part includes a guide part which guides the reagent container such that the storage medium of the reagent container set in the setting part thereof is located so as to face the radio wave communication part corresponding thereto. In this configuration, since the storage medium and the radio wave communication part can be located so as to face each other by the guide part, it is possible to more assuredly perform radio wave communication between the storage medium of the target reagent container and the radio wave communication part.

In the sample analyzer according to the above aspect, preferably, the radio wave blocking part is made of metal. In this configuration, radio waves from radio wave communication parts can be reflected at the radio wave blocking part made of metal. Thus, it is possible to easily prevent occurrence of erroneous reading and writing of information from and to the storage mediums of the reagent containers other than the target reagent container.

In this case, preferably, the radio wave blocking part is grounded. In this configuration, it is possible to suppress the radio wave blocking part itself made of metal from becoming a noise source. Thus, a good radio wave blocking effect can be obtained.

In the sample analyzer according to the above aspect, preferably, three or more reagent holder parts are provided as the plurality of reagent holder parts.

In this case, preferably, the plurality of reagent holder parts are arranged side by side in a line along a horizontal direction.

In the sample analyzer according to the above aspect, preferably, each radio wave communication part reads reagent-relating-information stored in the storage medium corresponding thereto and writes information into the storage medium, by transmitting and receiving a radio wave.

In this case, preferably, the reagent-relating-information includes at least one of a type, a lot number, and an expiration date of a reagent.

In the sample analyzer according to the above aspect, preferably, the sample is blood, and the sample analyzer is a blood analyzer which analyzes components in blood using the reagent contained in the reagent container.

In this case, preferably, the blood is whole blood, and the sample analyzer is a blood cell counter which stains blood cells included in the whole blood using staining reagent contained in the reagent container, and which counts the stained blood cells.

In the sample analyzer according to the above aspect, preferably, each setting part includes an aspiration tube which accesses the reagent in a reagent container by entering from above an opening provided in an upper face of the reagent container, each storage medium is provided on a side face of a reagent container, and each radio wave communication part is provided at a position close to a face, on which the storage medium is provided, of a reagent container set in the setting part corresponding thereto.

In this case, preferably, the setting part includes a cover which is movable in an up-down direction and which opens and closes a reagent container inlet, and the aspiration tube is configured to enter the reagent container, associated with a movement of the cover being closed.

In the sample analyzer according to the above aspect, preferably, each setting part is configured to hold a reagent container such that a bottom surface of the reagent container is inclined, and each aspiration tube is inserted into the reagent container such that a tip of the aspiration tube is located at a lower level side of the inclined bottom surface.

In order to achieve the above object, a reagent housing according to one aspect of the present invention is a reagent housing which holds a plurality of reagent containers each containing a reagent to be used in a sample analyzer, the reagent housing including: a reagent storage section in which a plurality of reagent holder parts are arranged, each of the reagent holder parts including a setting part in which a reagent container having a storage medium attached thereto is set, and a radio wave communication part which transmits and receives a radio wave to and from the storage medium of the reagent container set in the setting part; and a radio wave blocking part which blocks a radio wave communication path between the radio wave communication part of one of the reagent holder parts and the storage medium of the reagent container set in another reagent holder part that is adjacent to the one of the reagent holder parts.

These and other objects, features, aspects, and effects of the present invention will become more apparent from the following detailed description when taken in conjunction with the accompanying drawings.

DESCRIPTION OF THE PREFERRED EMBODIMENTS

Hereinafter, embodiments of the present invention will be described with reference to the drawings.

First, with reference to FIG. 1 to FIG. 10, an overall structure of a blood analysis system 1 according to an embodiment of the present invention will be described. In the present embodiment, a case will be described where the present invention is applied to measurement units, in a blood analysis system, which are an example of a sample analyzer.

Figure 1:
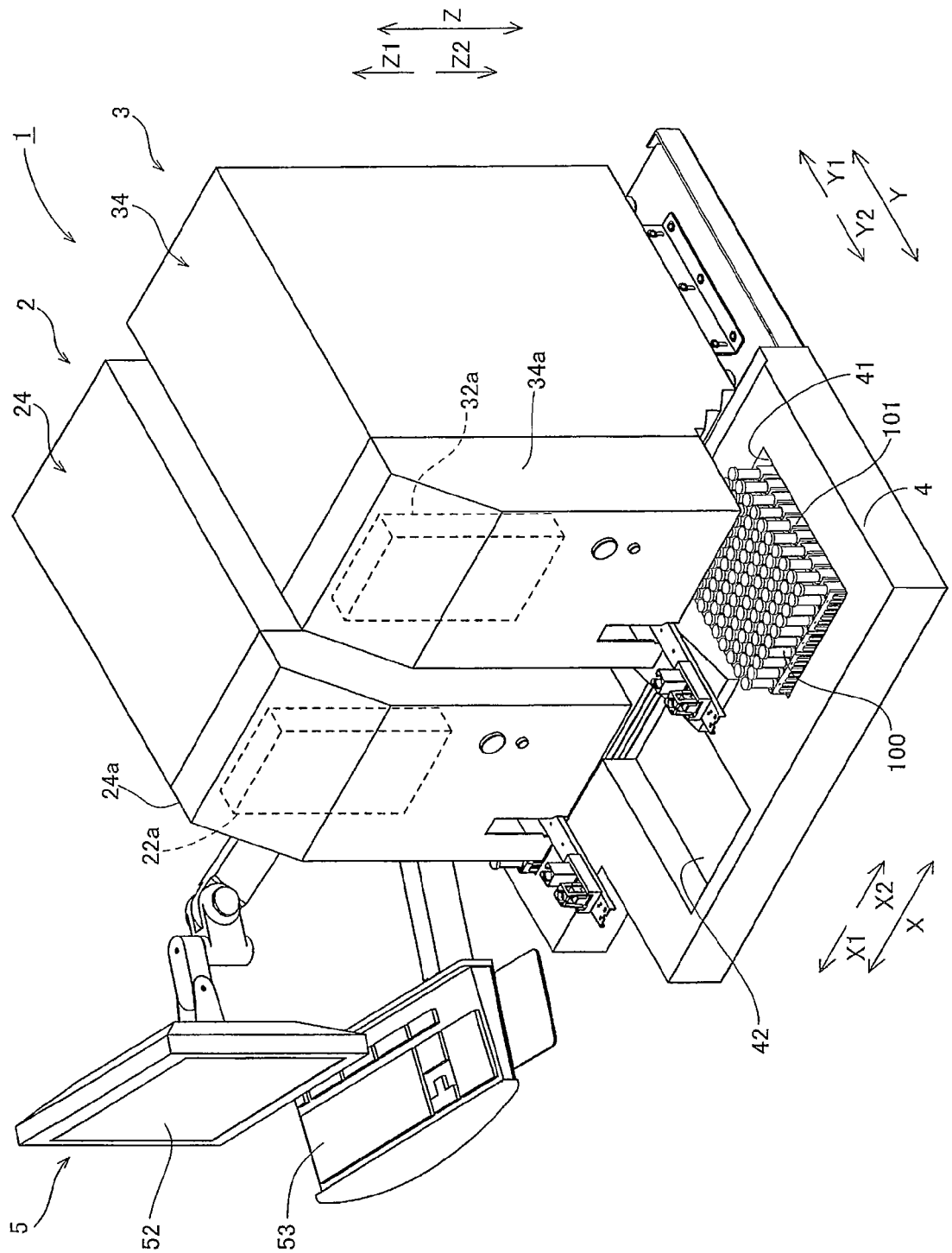
FIG. 1 is a perspective view showing a blood analysis system according to an embodiment of the present invention.

As shown in FIG. 1, the blood analysis system 1 according to the present embodiment includes: two measurement units which are a first measurement unit 3 arranged on an X2 direction side and a second measurement unit 2 arranged on an X1 direction side; a sample transporting apparatus (sampler) 4 arranged to the front (Y2 direction side) of the first measurement unit 3 and the second measurement unit 2; and a control device 5 electrically connected to the first measurement unit 3, the second measurement unit 2, and the sample transporting apparatus 4. Further, the blood analysis system 1 is connected to a host computer 6 (see FIG. 2) via the control device 5.

Figure 2:
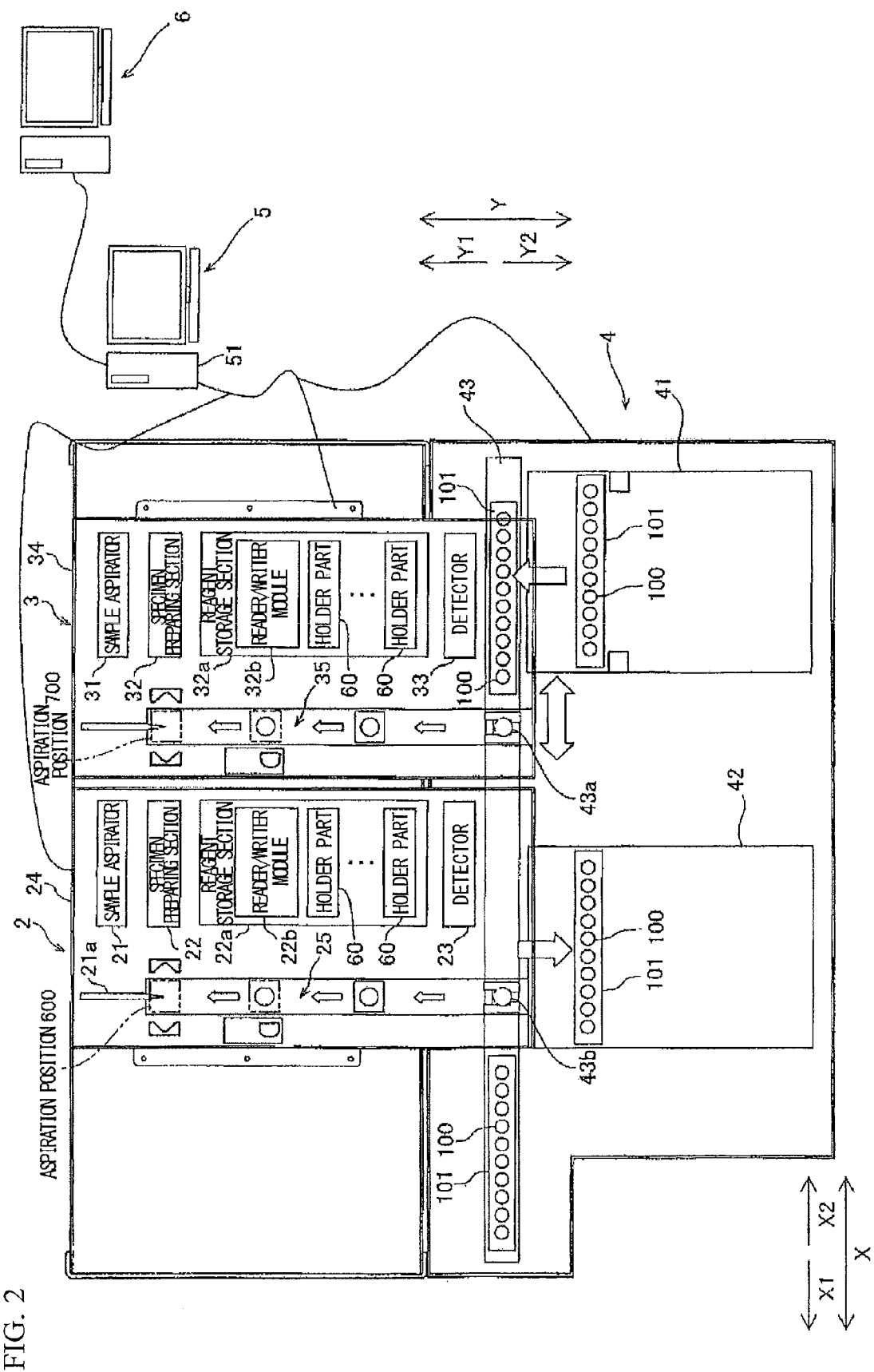
FIG. 2 is a schematic diagram showing a structure of the blood analysis system including a first measurement unit and a second measurement unit according to the embodiment shown in FIG. 1.

As shown in FIG. 1 and FIG. 2, the first measurement unit 3 and the second measurement unit 2 are measurement units of substantially the same type and are arranged adjacent to each other. Specifically, in the present embodiment, the second measurement unit 2 uses the same measurement principle as that of the first measurement unit 3 to measure a sample for the same measurement items. Further, the second measurement unit 2 also measures a sample for measurement items that are not analyzed by the first measurement unit 3. As shown in FIG. 2, the second measurement unit 2 and the first measurement unit 3 respectively include sample aspirators 21 and 31 which aspirate blood being samples from sample containers 100, specimen preparing sections 22 and 32 which prepare specimens for detection from the blood aspirated by the sample aspirators 21 and 31, and detectors 23 and 33 which detect blood cells in the blood from the specimens for detection prepared by the specimen preparing sections 22 and 32.

Further, as shown in FIG. 2, the second measurement unit 2 and the first measurement unit 3 further respectively include: unit covers 24 and 34 which house therein the sample aspirators 21 and 31, the specimen preparing sections 22 and 32, and the like; and sample container transporters 25 and 35 which take in sample containers 100 inside the unit covers 24 and 34 and transport the sample containers 100 to aspiration positions 600 and 700 at which the sample aspirators 21 and 31 aspirate the blood. Since the first measurement unit 3 and the second measurement unit 2 are measurement units of substantially the same type as described above, the second measurement unit 2 will be described hereinafter, and description of the first measurement unit 3 is omitted.

The sample aspirator 21 is configured to aspirate, by a predetermined amount, a sample by means of a piercer 21a from a sample container 100 containing a sample (blood) to be analyzed. Further, the sample aspirator 21 has a function of supplying the sample aspirated by the predetermined amount, to the specimen preparing section 22.

The specimen preparing section 22 is configured to mix together the sample supplied from the sample aspirator 21 and predetermined amounts of reagents contained in reagent containers 90 described below. In the specimen preparing section 22, a plurality of types of reagents (e.g., staining solution) corresponding to measurement items are used, and after mixing of a sample and reagents together and the reaction process therebetween, a plurality of types of test specimens corresponding to various types of measurement items are prepared. Then, each prepared test specimen is supplied to the detector 23.

The detector 23 has a function of performing RBC detection (detection of red blood cells) and PLT detection (detection of platelets) on the test specimen supplied from the specimen preparing section 22 by using a sheath flow DC detection method, and performing HGB detection (detection of hemoglobin in blood) by using an SLS-hemoglobin method. Further, the detector 23 has a function of performing WBC detection (detection of white blood cells) by flow cytometry using semiconductor laser. A detection result obtained by the detector 23 is transmitted to the control device 5 as measurement data (measurement result) of the sample.

The sample container transporter 25 is configured to, when a sample container 100 has been transported to a predetermined loading position 43b by the sample transporting apparatus 4, take in the sample container 100 inside the second measurement unit 2 and transport the sample container 100 to the aspiration position 600.

As shown in FIG. 1 and FIG. 2, the sample transporting apparatus 4 includes: a pre-measurement rack holding part 41 where a plurality of racks 101 are arranged, each rack 101 holding sample containers 100 containing samples before being subjected to measurement; a post-measurement rack holding part 42 where a plurality of racks 101 are arranged, each rack 101 holding sample containers 100 containing samples after being subjected to measurement; and a rack transporter 43 which horizontally and linearly moves each rack 101 in the directions indicated by arrows X1 and X2.

As shown in FIG. 2, the pre-measurement rack holding part 41 is configured to move the racks 101 arranged in the pre-measurement rack holding part 41 in the Y1 direction, and to push out the racks 101 one by one onto the rack transporter 43.

The rack transporter 43 is configured to, by transporting a rack 101, locate a predetermined sample container 100 held in the rack 101, at a loading position 43a at which the first measurement unit 3 takes in the sample, and at the loading position 43b at which the second measurement unit 2 takes in the sample. Further, the rack transporter 43 has a function of transporting a rack 101 holding sample containers 100 containing samples having subjected to measurement, to the post-measurement rack holding part 42.

As shown in FIG. 1 and FIG. 2, the control device 5 is implemented by a personal computer (PC) and the like, and is mainly composed of a controller 51 (see FIG. 2) including a CPU, a ROM, a RAM, and the like; a display section 52; and an input device 53. The controller 51 controls operations of component sections of the first measurement unit 3, the second measurement unit 2, and the sample transporting apparatus 4. Further, the controller 51 is configured to analyze analysis-target components, by using measurement results transmitted from the first measurement unit 3 and the second measurement unit 2, and to obtain analysis results (red blood cell count, platelet count, amount of hemoglobin, while blood cell count, etc.). The display section 52 is provided in order to display analysis results and the like obtained by analyzing digital signal data transmitted from the first measurement unit 3 and the second measurement unit 2.

Figure 3:
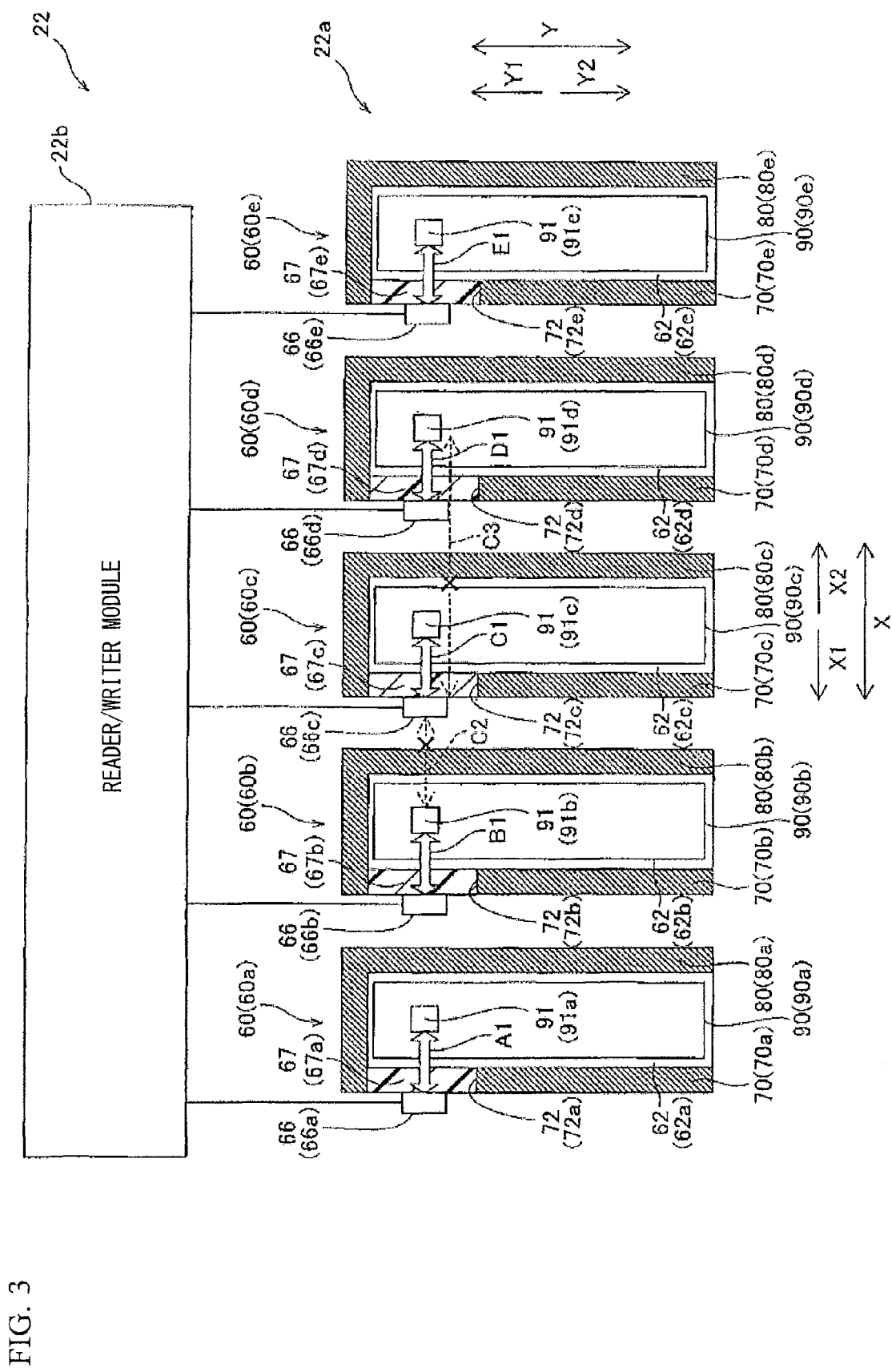
FIG. 3 is a schematic diagram showing a structure of a reagent storage section of the second measurement unit according to the embodiment shown in FIG. 2.

As shown in FIG. 3, the second measurement unit 2 includes: a reagent storage section 22a which holds a plurality of reagent containers 90 each containing a predetermined amount of reagent; and a reader/writer module 22b which performs reading/writing of an RFID (Radio Frequency Identification) tag 91 attached to each reagent container 90, the reagent storage section 22a and the reader/writer module 22b being provided inside the unit cover 24 (see FIG. 1). As shown in FIG. 1, a front cover 24a which is openable is provided to the front of the unit cover 24. The reagent storage section 22a is arranged in an upper front portion of the second measurement unit 2, and when the front cover 24a is open, the reagent storage section 22a is exposed to outside, thereby allowing replacement of reagents.

Figure 4:
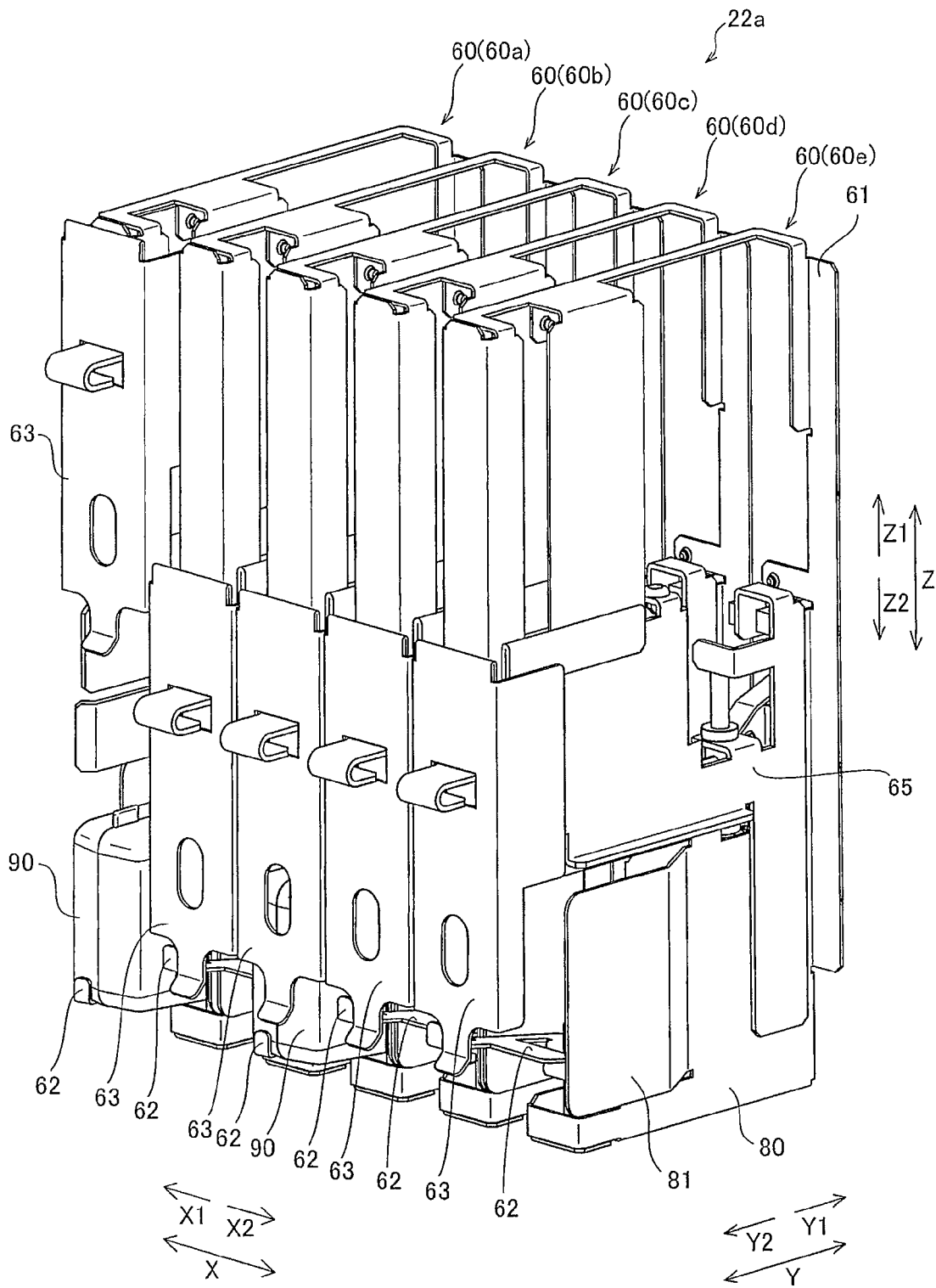
FIG. 4 is a perspective view showing the reagent storage section of the second measurement unit according to the embodiment shown in FIG. 3.

As shown in FIG. 4, the reagent storage section 22a includes five holder parts 60 (60a to 60e) linearly arranged side by side along the width direction (X direction). In each holder part 60 (60a to 60e), one reagent container 90 is detachably set. Thus, the reagent storage section 22a is configured to hold five (five types of) reagent containers 90 in total. The reagent containers 90 held in the reagent storage section 22a respectively contain different types of reagents in order to allow the detector 23 to measure a plurality of measurement items.

Figure 5:
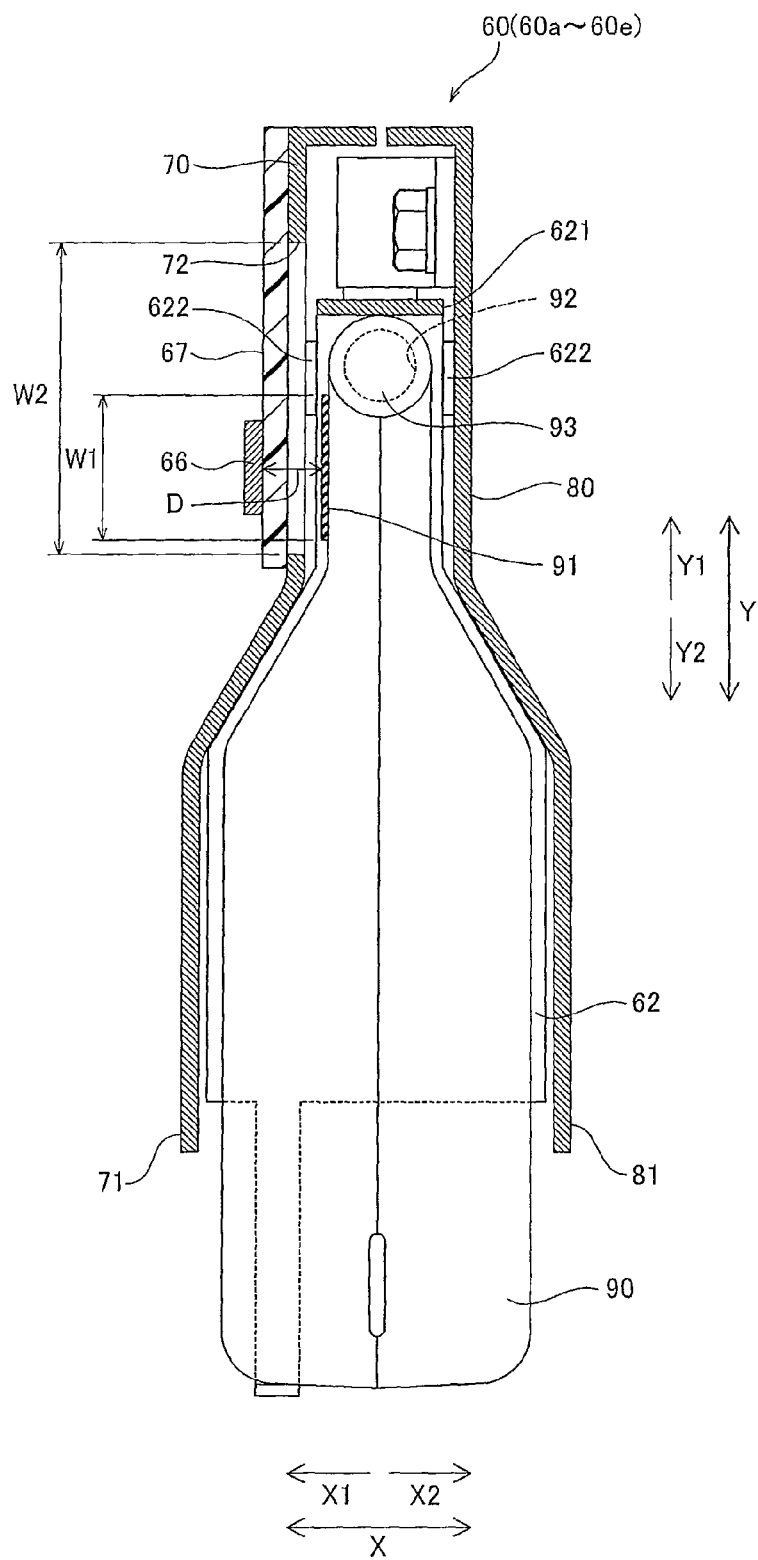
FIG. 5 is a plane cross-sectional view schematically showing a state where a reagent container is set in a holder part of the reagent storage section shown in FIG. 4.

As shown in FIG. 5, each reagent container 90 has a leading portion of a small width, and is provided with an entrance part 92 where an opening is formed on an upper end (upper face) of the leading portion. The entrance part 92 is sealed with a sealing member 93 made of aluminum foil or the like. Further, a sheet-like RFID tag 91 is attached to one side face of the leading portion of the reagent container 90. The RFID tag 91 includes an antenna circuit and a storage circuit capable of writing and reading of information.

Figure 6:
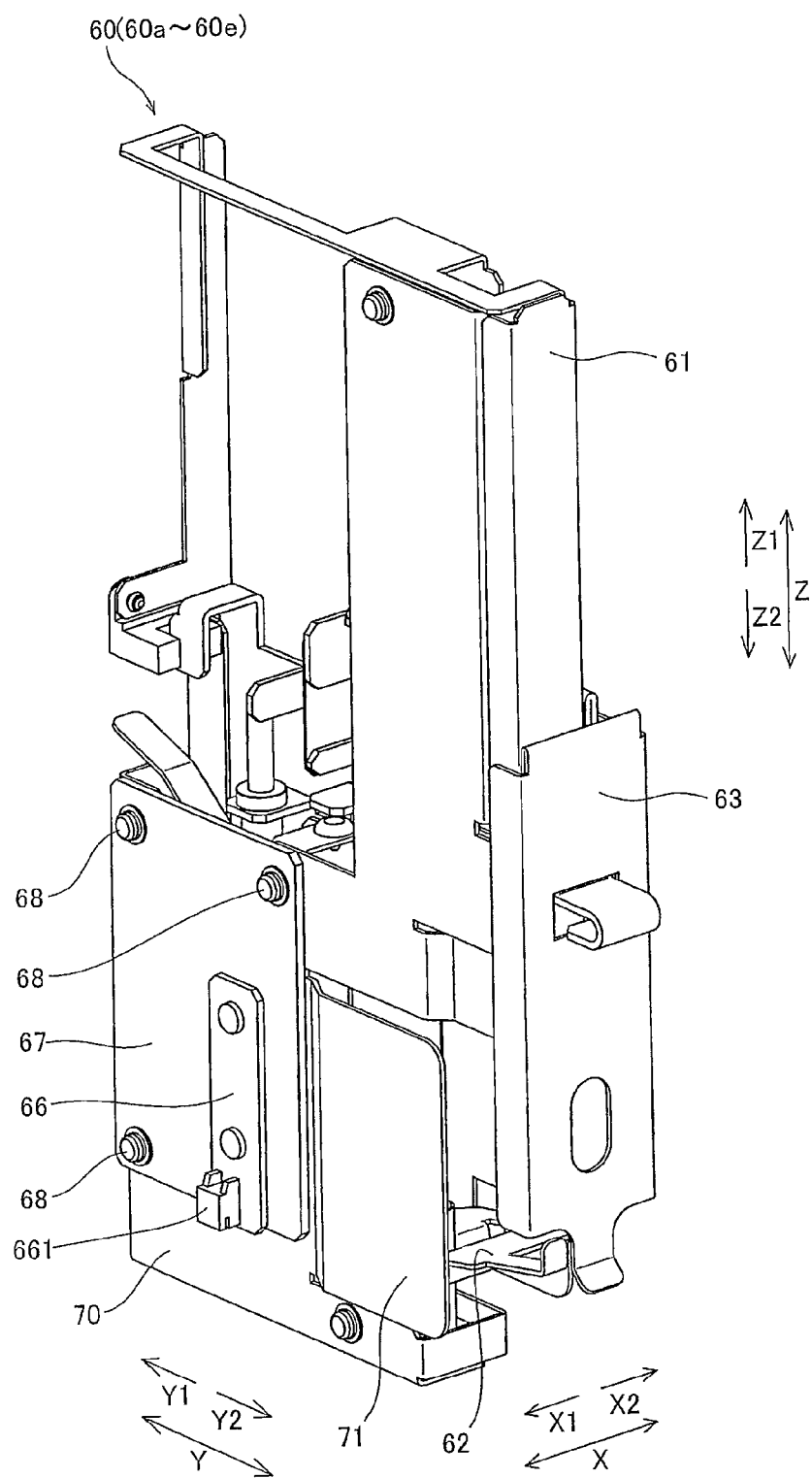
FIG. 6 is a perspective view showing the holder part of the reagent storage section shown in FIG. 4, viewed from a left face part side.
Figure 7:
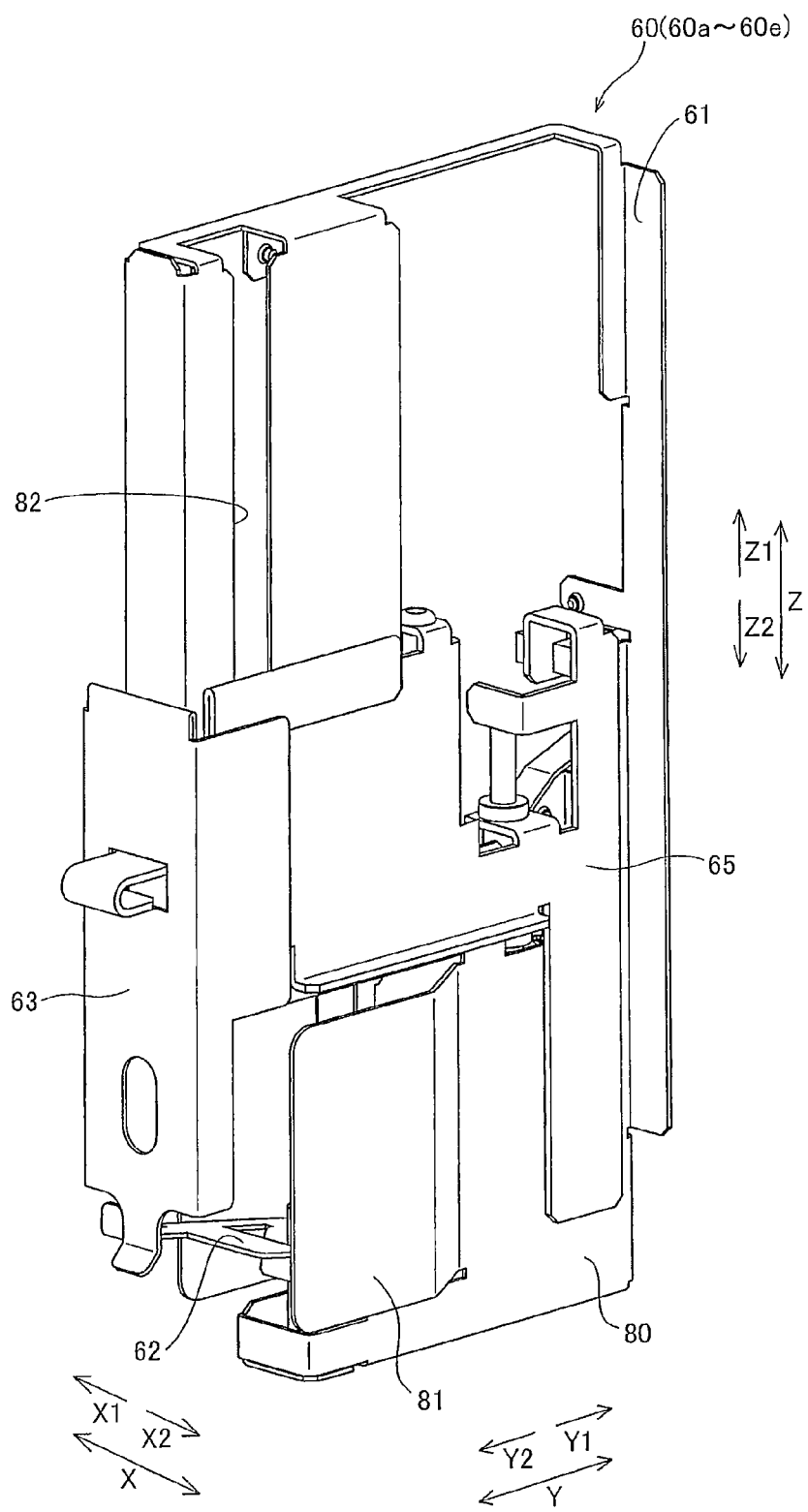
FIG. 7 is a perspective view showing the holder part of the reagent storage section shown in FIG. 4, viewed from a right face part side.
Figure 8:
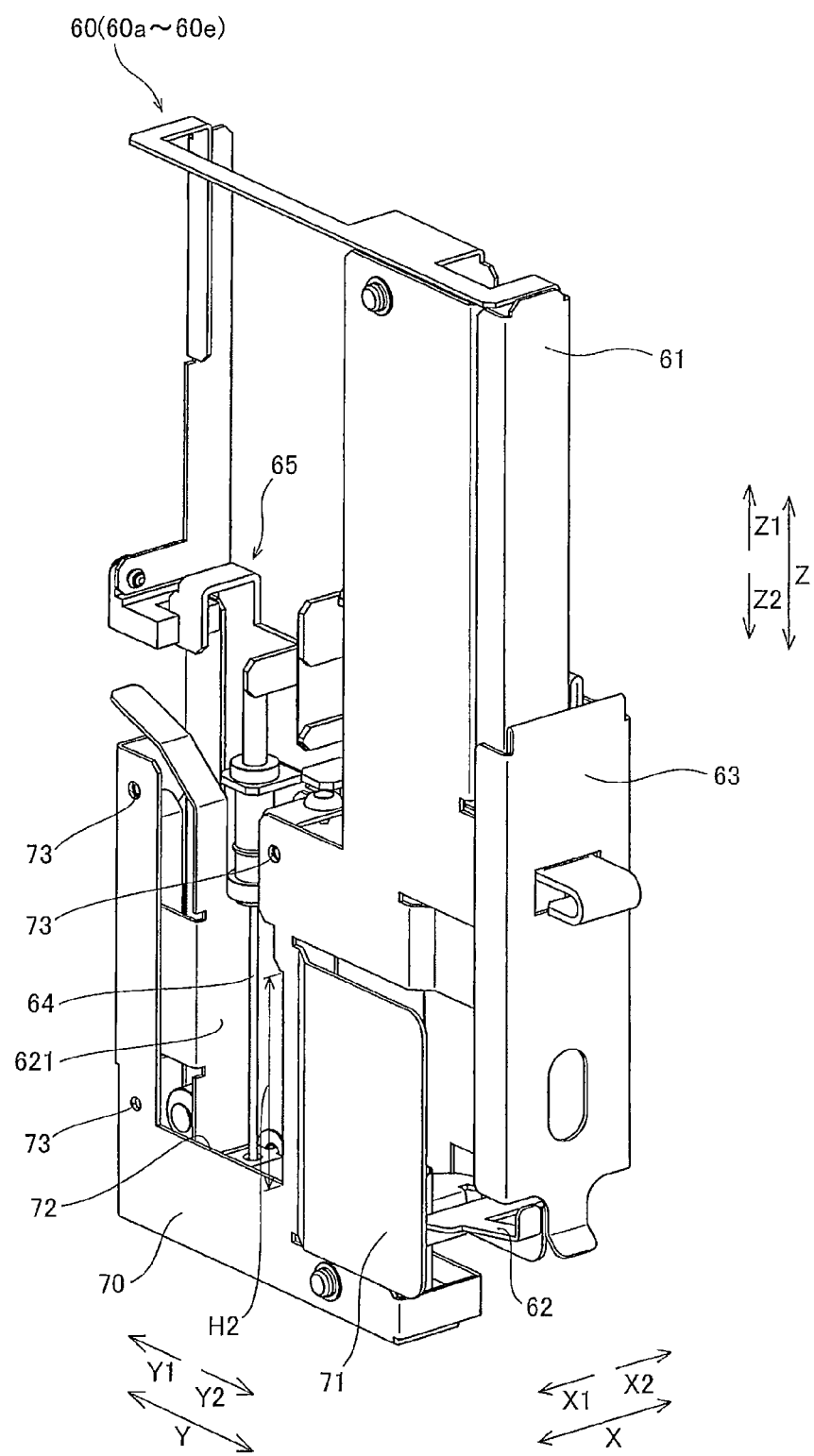
FIG. 8 is a perspective view showing the holder part shown in FIG. 6 without a protection member.

Each of the five holder parts 60 (60a to 60e) has the same structure. As shown in FIG. 6 to FIG. 8, each holder part 60 includes a chassis 61 made of metal, a setting part 62 in which a reagent container 90 is set, a cover 63 for exposing and hiding the inside of the chassis 61, a piercer 64 which aspirates a reagent in the reagent container 90 (see FIG. 8), and a piercer raising/lowering mechanism 65.

In the present embodiment, as shown in FIG. 6, the holder part 60 is provided with an antenna part 66 connected to the reader/writer module 22b so as to be able to transmit/receive an electric signal therebetween. The antenna part 66 (also referred to as a radio wave communication part) transmits/receives a radio wave to/from the RFID tag 91 of the reagent container 90. By the antenna part 66 of the holder part 60 and the RFID tag 91 of the reagent container 90 (see FIG. 5) performing noncontact short distance wireless communication therebetween using a radio wave, reading/writing of reagent information is performed. In the RFID tag 91, for example, reagent information such as the type, the lot number, and the expiration date of the reagent contained in the reagent container 90 is stored. The reagent information is read/written by the control device 5 (see FIG. 1) by means of the reader/writer module 22b, and is used for management of the reagent.

The antenna part 66 is connected to the reader/writer module 22b via a connector part 661. The antenna part 66 has a function of transmitting a radio wave including a control signal to an RFID tag 91 in the vicinity thereof in accordance with a signal from the reader/writer module 22b (see FIG. 3), and of receiving a radio wave including process result information corresponding to the control signal, from the RFID tag 91.

Specifically, when writing information, the reader/writer module 22b converts information to be written in the RFID tag 91, into an electric signal, and sends the electric signal to the antenna part 66. The antenna part 66 converts the electric signal from the reader/writer module 22b into a radio wave, and transmits the converted radio wave to the RFID tag 91. The RFID tag 91 induces an electric power from the transmitted radio wave, and stores information included in the transmitted radio wave into its storage circuit, by using this electric power. Accordingly, information is written into the RFID tag 91. On the other hand, when reading information, the antenna part 66 transmits a radio wave to the RFID tag 91, thereby causing an electric power to be induced in the RFID tag 91. The RFID tag 91 takes out information stored in the storage circuit by using this electric power, and transmits via its antenna circuit the information to the antenna part 66 using a radio wave. The antenna part 66 converts the received radio wave into an electric signal, and sends the electric signal to the reader/writer module 22b. Accordingly, information from the RFID tag 91 is read.

The communication distance of the antenna part 66 defers depending on the frequency band of the radio wave used, and the like, and is about several centimeters in the present embodiment. Further, as shown in FIG. 5, a distance D between the antenna part 66 and the RFID tag 91 of the reagent container 90 set in the setting part 62 is about 1 cm.

As shown in FIG. 5 to FIG. 7, each chassis 61 has a left face part 70 on the X1 direction side and a right face part 80 on the X1 direction side. The chassis 61 (the left face part 70 and the right face part 80) is formed by a plate member made of metal. In the present embodiment, the chassis 61 is made of stainless steel (SUS430). The left face part 70 and the right face part 80 of the chassis 61 respectively include guide parts 71 and 81 integrally formed therein. It should be noted that, inside the unit cover 24, a metallic frame (not shown) holding components included in the second measurement unit 2 is provided. The chassis 61 is fixed to this frame and is grounded via the frame.

Here, as shown in FIG. 5 and FIG. 8, the left face part 70 is provided with a cutout part 72 formed by cutting out a predetermined portion in a lower part on a depth side of the left face part 70, into a substantially U shape. As shown in FIG. 5, the cutout part 72 is provided such that, in a state where the reagent container 90 is set in the setting part 62 (i.e., in a state where the reagent container 90 is set at a set position described below), the RFID tag 91 of the reagent container 90 is exposed through the chassis 61 on the left face part 70 side. Therefore, the cutout part 72 is formed at a position facing the RFID tag 91 of the reagent container 90 set in the setting part 62, such that the size of the cutout part 72 (the area of the cut out portion) is greater than the size (plane area) of the RFID tag 91. That is, the cutout part 72 has a width W2 (see FIG. 5) and a height H2 (see FIG. 8), and the width W2 and the height H2 are greater than a width W1 (see FIG. 5) and a height H1 (the length of the long side, see FIG. 10) of the RFID tag 91, respectively. The cutout part 72 is provided in order to allow a radio wave to pass therethrough between the antenna part 66 and the setting part 62.

Further, as shown in FIG. 5 and FIG. 6, the left face part 70 of the chassis 61 is provided with a protection member 67 so as to cover the cutout part 72. The protection member 67 is formed from a resin material that allows a radio wave to pass therethrough. In the present embodiment, the protection member 67 is formed by a plate-like member made of polyacetal. The protection member 67 is fixed to the left face part 70 by means of a resin screw member 68 which is threadedly engaged with a threaded hole 73 (see FIG. 8). In the present embodiment, the antenna part 66 is attached to a surface of the protection member 67, on a side (X1 direction side) opposite to the cutout part 72. Thus, the antenna part 66 is configured to communicate with the RFID tag 91 of the reagent container 90 set in the setting part 62, via the protection member 67 which allows a radio wave to pass therethrough and the cutout part 72 of the left face part 70.

Figure 10:
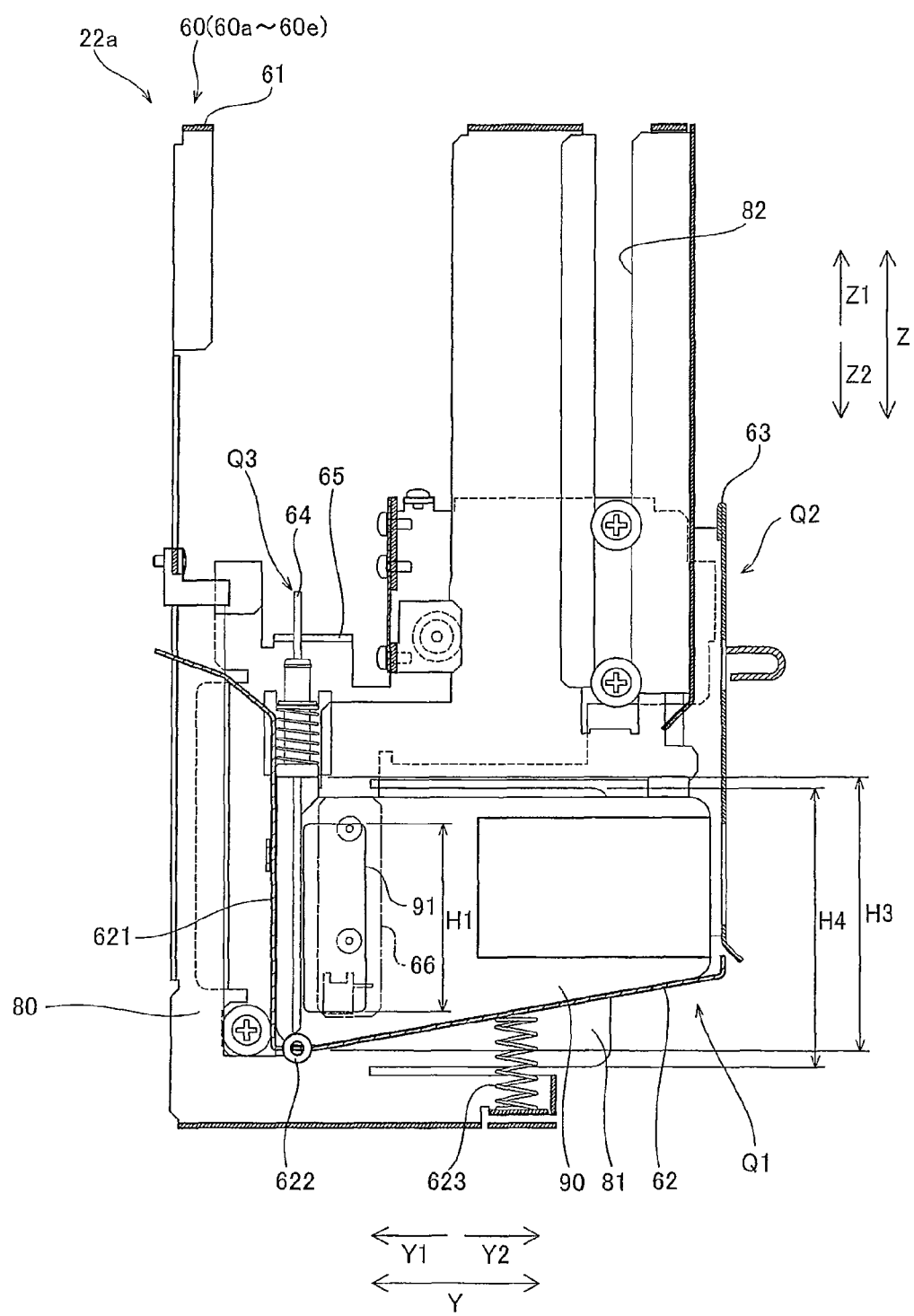
FIG. 10 illustrates a state where a reagent container is set, in the longitudinal sectional view of the holder part shown in FIG. 9.

As shown in FIG. 5, the guide parts 71 and 81 are provided so as to face each other in the X direction, relative to the setting part 62. Further, the guide parts 71 and 81 respectively have bent shapes corresponding to the tapered external shape of the reagent container 90 set in the setting part 62. Thus, the reagent container 90 can be inserted into the setting part 62, only from the leading portion side where the entrance part 92 is provided. The guide parts 71 and 81 guide both side faces of the reagent container 90 such that the RFID tag 91 of the reagent container 90 is located at a position and an orientation where the RFID tag 91 just faces the antenna part 66 when the reagent container 90 is set in the setting part 62. Further, as shown in FIG. 10, the guide parts 71 and 81 each have a height H4, which is substantially equal to a maximum height (the length from the bottom surface of the leading portion to the upper end surface thereof) H3 of the reagent container 90. Therefore, when the reagent container 90 is set in the setting part 62, the guide parts 71 and 81 are respectively positioned so as to cover the entirety of the side faces of the reagent container 90.

As shown in FIG. 5, in the present embodiment, each of the five holder parts 60 (60a to 60e) arranged side by side along a predetermined direction (X direction) is configured such that, relative to the RFID tag 91 when the reagent container 90 is set in the setting part 62, the antenna part 66 is arranged on the left side (X1 direction side) via the cutout part 72, and the right face part 80 of the chassis 61 is arranged on the right side (X2 direction side). As described above, in order to perform communication with the RFID tag 91, the antenna part 66 emits a radio wave to the vicinity thereof. In order for the antenna part 66 of each holder part 60 (60a to 60e) to appropriately communicate with its corresponding RFID tag 91 of the reagent container 90 set in the holder part 60 (60a to 60e), it is necessary to assuredly block communication with the RFID tags 91 of the reagent containers 90 set in its adjacent holder parts. Therefore, in the present embodiment, the left face part 70 and the right face part 80 of the chassis 61 are configured to function as a radio wave blocking part which blocks radio waves generated from antenna parts 66. That is, the left face part 70 and the right face part 80 each made of metal are configured to reflect unnecessary radio waves generated from antenna parts 66.

Further, in a state where the reagent container 90 is set in the setting part 62, it is configured such that the reagent container 90 is surrounded, except a rear end portion thereof (Y2 direction end portion), by the left face part 70 (and the guide part 71) and the right face part 80 (and the guide part 81). In addition, it is configured such that the guide parts 71 and 81 integrally provided in the left face part 70 and the right face part 80 also function as the radio wave blocking part.

In the present embodiment, the antenna part 66 of each of the five holder parts 60 (60a to 60e) can communicate (read and write information) only with the RFID tag 91 of the reagent container 90 set in its corresponding setting part 62 so as to face the antenna part 66. On the other hand, with respect to the antenna part 66 of each holder parts 60 (60a to 60e), a communication path between this antenna part 66 and the RFID tag 91 of the reagent container 90 set in each of its adjacent other holder parts 60 is blocked by a corresponding right face part 80, and thus, the antenna part 66 cannot communicate with the RFID tag 91 of the reagent container 90 in those other holder parts 60. The communication paths between the antenna parts 66 and the RFID tags 91 will be described later in detail.

Figure 9:
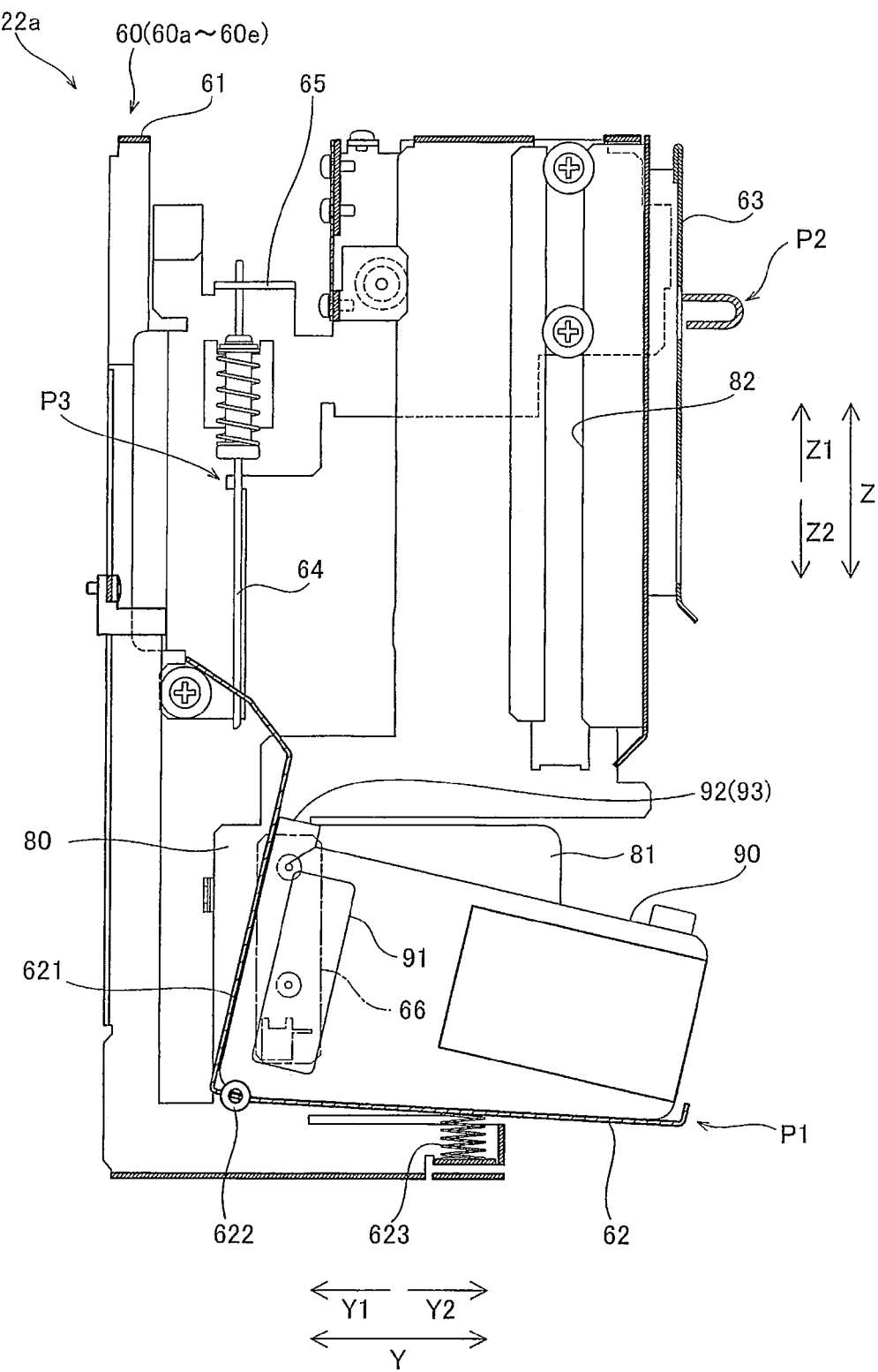
FIG. 9 is a longitudinal sectional view schematically showing an internal structure of the holder part of the reagent storage section shown in FIG. 4.

As shown in FIG. 5 to FIG. 8, the setting part 62 is provided in a lower part of the chassis 61. When seen in a plane view, the setting part 62 has a shape corresponding to the reagent container 90, and is capable of having the reagent container 90 set therein. Further, as shown in FIG. 9 and FIG. 10, the setting part 62 is provided with a stopper 621 in such a manner as to extend upward from a deepest portion of the setting part 62. The stopper 621 has a function of locating the reagent container 90 at a predetermined position on the setting part 62 by coming into contact with the leading portion of the reagent container 90 when the reagent container 90 is set. Further, the setting part 62 includes a rotation shaft 622 and a spring member 623. The setting part 62 is configured to rotate about the rotation shaft 622, associated with opening/closing (raising/lowering) of the cover 63, under a force applied by the spring member 623. Accordingly, the setting part 62 can rotate between a mounting position P1 (see FIG. 9) at which the upper face of the setting part 62 (the setting surface for the reagent container 90) becomes substantially horizontal while the cover 63 is open, and a set position Q1 (see FIG. 10) at which the piercer 64 can enter the reagent container 90 through the entrance part 92 of the reagent container 90 set in the setting part 62 while the cover 63 is closed. At the set position Q1, the upper face of the reagent container 90 set in the setting part 62 becomes substantially horizontal, and the RFID tag 91 of the reagent container 90 is located at a position (see FIG. 5) facing the antenna part 66.

As shown in FIG. 6 and FIG. 7, the cover 63 is located to the front of (arrow Y2 direction side) each holder part 60 (the chassis 61), and is attached to the piercer raising/lowering mechanism 65. The piercer raising/lowering mechanism 65 allows the cover 63 to move between a raised position P2 (see FIG. 9) at which the setting part 62 is open, and a lowered position Q2 (see FIG. 10) at which the setting part 62 is covered (closed).

The piercer 64 is a tubular member extending in the up-down direction. As shown in FIG. 9, the piercer 64 is arranged at an upper position in a deepest portion (arrow Y2 direction side) of the setting part 62, and is configured to be moved in the vertical direction (Z direction) by the piercer raising/lowering mechanism 65 holding the piercer 64. Further, the piercer 64 has a sharp tip so as to be able to pass through (puncture) the sealing member 93 of the reagent container 90. Accordingly, the piercer 64 can enter the reagent container 90 through the entrance part 92 at the upper end of the leading portion of the reagent container 90 inserted to the depth side of the setting part 62. As a result, the piercer 64 can aspirate the reagent in the reagent container 90. The reagent aspirated via the piercer 64 is mixed with the sample in the specimen preparing section 22.

The piercer raising/lowering mechanism 65 is configured to hold the piercer 64 and the cover 63. Further, the piercer raising/lowering mechanism 65 is engaged with a movement groove 82 provided in the right face part 80 of the chassis 61, so as to be movable in the vertical direction (Z direction). Accordingly, the piercer raising/lowering mechanism 65 is configured to integrally move the piercer 64 in the vertical direction (Z direction), associated with opening/closing (ascending/descending movement) of the cover 63. Then, as shown in FIG. 9, in a state where the cover 63 is located at the raised position P2, the piercer 64 is located at a raised position P3 above the setting part 62 (above the reagent container 90). As shown in FIG. 10, in a state the cover 63 is located at the lowered position Q2, the piercer 64 is located at a lowered position Q3 at which the tip of the piercer 64 is located close to the inner bottom directly below the entrance part 92 of the reagent container 90.

Next, with reference to FIG. 3 and FIG. 5, the communication paths between the antenna parts 66 and the RFID tags 91 will be described. Here, the components of the holder parts 60a to 60e will be referred to as the setting parts 62a to 62e, the antenna parts 66a to 66e, the protection members 67a to 67e, the left face parts 70a to 70e, the cutout parts 72a to 72e, the right face parts 80a to 80e, the reagent containers 90a to 90e, and the RFID tags 91a to 91e, respectively.

As shown in FIG. 3, when focusing on the holder part 60c at the center, for example, the antenna part 66c of the holder part 60c can communicate (read and write information) through a communication path C1 via the protection member 67c and the cutout part 72c, with the RFID tag 91c of the reagent container 90c set in the holder part 60c.

On the other hand, between the RFID tag 91b of the reagent container 90b set in the holder part 60b adjacent to the holder part 60c in the X1 direction and the antenna part 66c of the holder part 60c, the right face part 80b is arranged as the radio wave blocking part of the holder part 60b. Accordingly, a communication path C2 between the antenna part 66c of the holder part 60c and the RFID tag 91b of the reagent container 90b in the holder part 60b is blocked (radio waves are reflected) by the right face part 80b of the holder part 60b.

Further, a communication path C3 between the RFID tag 91d of the reagent container 90d in the holder part 60d adjacent to the holder part 60c in the X2 direction and the antenna part 66c of the holder part 60c is blocked by the right face part 80c of the holder part 60c itself (and the guide part 81, see FIG. 5). As a result, the antenna part 66c of the holder part 60c can communicate only with the RFID tag 91c of its corresponding reagent container 90c set in the setting part 62c of the holder part 60c. It should be noted that the radio wave from the antenna part 66c also spreads in directions other than the shown communication paths C1 to C3. In the present embodiment, in the respective holder parts 60a to 60e, the left face parts 70a to 70e (the guide part 71, see FIG. 5) and the right face parts 80a to 80e (the guide part 81, see FIG. 5) are provided so as to respectively surround the reagent containers 90a to 90e. Therefore, a radio wave from the antenna part 66c to other RFID tags 90a, 90b, 90d, and 90e (communication paths) can be more assuredly blocked.

As described above, the antenna parts 66a to 66e of the holder parts 60a to 60e can perform communication (reading and writing of information) only through the communication paths A1 to E1 which correspond to the RFID tags 91a to 91e of their corresponding reagent containers 90a to 90e set in the setting parts 62a to 62e, respectively. Although no radio wave blocking part exists to the X1 direction side of the holder part 60a arranged at the end in the X1 direction, since no adjacent holder part exists, there is no risk of communication performed with the RFID tag of a reagent container in another holder part.

Next, with reference to FIG. 1, FIG. 3, FIG. 5, FIG. 9, and FIG. 10, an operation of setting a reagent container 90 onto the reagent storage section 22a (the holder part 60) of the second measurement unit 2 and the first measurement unit 3 according to the present embodiment will be described. Since the operations of setting a reagent container 90 (90a to 90e) to the holder parts 60a to 60e are the same, description thereof for each of the holder parts 60a to 60e is omitted.

First, a user opens the front cover 24a (see FIG. 1), and locates the cover 63 at the raised position P2 (see FIG. 9) to make the setting part 62 open. At this time, as shown in FIG. 9, associated with the cover 63 being raised, the setting part 62 is located at the mounting position P1 at which the setting surface for the reagent container 90 becomes horizontal. The piercer 64 is located at the raised position P3 above the setting part 62, associated with the cover 63 being located at the raised position P2.

Next, the user mounts the reagent container 90 on the setting part 62. At this time, the user causes the reagent container 90 to enter toward the depth side (Y1 direction) of the setting part 62, from the leading portion side of the reagent container 90. At this time, the reagent container 90 is inserted to a predetermined position at which the reagent container 90 comes into contact with the stopper 621 of the setting part 62, while the entirety of both side faces of the reagent container 90 is being guided along the pair of the guide parts 71 and 81 (see FIG. 5) which have shapes corresponding to the shape of the reagent container 90.

Next, the user moves (lowers) the cover 63 from the raised position P2 to the lowered position Q2 (see FIG. 10) to close the setting part 62. At this time, associated with the cover 63 being lowered, the setting part 62 rotates to the set position Q1. As a result, the RFID tag 91 of the reagent container 90 is located at a position facing the antenna part 66.

When the RFID tag 91 of the reagent container 90 is located at the position facing the antenna part 66, the control device 5 (see FIG. 1) reads reagent information stored in the RFID tag 91 or writes new information into the RFID tag 91 by means of the reader/writer module 22b (see FIG. 3). At this time, the antenna part 66 and the RFID tag 91 communicate with each other through short distance wireless communication.

Since the piercer 64 is also lowered associated with the lowering of the cover 63, the piercer 64 passes through the sealing member 93 sealing the entrance part 92 of the reagent container 90 and enters the reagent container 90 via the entrance part 92. When the cover 63 is located at the lowered position Q2 by the user, the piercer 64 is located at the lowered position Q3 at which the tip of the piercer 64 is located near the bottom in the reagent container 90. Accordingly, it becomes possible to aspirate the reagent in the reagent container 90 via the piercer 64.

Thus, the operation of setting the reagent container 90 onto the reagent storage section 22a (the holder part 60) is completed.

In the present embodiment, as described above, the right face parts 80 (80b and 80c) are provided which block the radio wave communication paths between the antenna part 66 (66c) of the one holder part 60 (e.g., 60c) and the RFID tags 91 (91b and 91d) of the reagent containers 90 (90b and 90d) arranged in other holder parts 60 (60b and 60d) adjacent to the one holder part 60 (60c). Accordingly, of the radio wave emitted from the antenna part 66c of the one holder part 60c, the radio wave advancing toward the RFID tags 91b and 91d of the reagent containers 90b and 90d set in those other adjacent holder parts 60b and 60d can be blocked by the right face parts 80b and 80c. As a result, in each holder part 60, it is possible to read/write information from/to the RFID tag 91 of the reagent container 90 set in its own setting part 62, and at the same time, it is possible to prevent occurrence of reading/writing information from/to the RFID tags 91 of the reagent containers 90 in other adjacent holder parts. Accordingly, it is possible to prevent occurrence of erroneous reading/writing of information from/to the RFID tags 91 of the reagent containers 90 other than the target reagent container 90.

In the present embodiment, as described above, the right face parts 80 (80b and 80c) are provided between the antenna part 66 (66c) of the one holder part 60 (e.g., 60c) and the RFID tags 91 (91b and 91d) of the reagent containers 90 (90b and 90d) set in the setting parts 62 (62b and 62d) of other holder parts 60 (60b and 60d) adjacent to the one holder part 60 (60c). In this configuration, the radio wave communication paths (C2 and C3 in FIG. 3) between the antenna part 66 (66c) of the one holder part 60 (60c) and the RFID tags 91 (91b and 91d) of the reagent containers 90 (90b and 90d) set in those other holder parts 60 (60b and 60d) adjacent to the one holder part 60 (60c) can be assuredly blocked.

In the present embodiment, as described above, each holder part 60 is formed from a conductive material (stainless steel) provided so as to surround the reagent container 90 set in the setting part 62, and the conductive material forms the left face part 70 and the right face part 80. In this configuration, the left face part 70 and the right face part 80 formed from the conductive material having a shape surrounding the reagent container 90 set in the setting part 62 can more assuredly prevent occurrence of reading/writing of information from/to RFID tags 91 of non-target reagent containers 90 set in other holder parts 60.

In the present embodiment, as described above, in the left face part 70 of each holder part 60 formed from a conductive material, the cutout part 72 is formed at a position corresponding to the antenna part 66. In this configuration, it is possible to assuredly perform reading/writing of information from/to the RFID tag 91 of the target reagent container 90, via the cutout part 72 formed in the conductive material (the left face part 70).

Meanwhile, in a case where a window-like opening part is formed in the left face part 70 formed from the conductive material, for example, a conductive body (metal) loop will be formed around the opening part. Thus, the loop portion around the opening part may serve as if it were an antenna due to electromagnetic induction or the like. As a result, communication between the antenna part 66 and the RFID tag 91 may be disturbed. In contrast, in the present embodiment, the cutout part 72 is formed at the position corresponding to the antenna part 66, and thus, formation of the conductive body (metal) loop around the cutout part 72 (on the left face part 70) can be prevented. Therefore, communication can be performed in a good condition between the antenna part 66 and the RFID tag 91 via the cutout part 72.

In the present embodiment, as described above, the protection member 67 is provided so as to cover the cutout part 72, and is formed from a radio wave transmissive material that allows a radio wave to pass therethrough. In this configuration, the space between the antenna part 66 and the reagent container 90 set in the setting part 62 can be separated by the protection member 67 provided so as to cover the cutout part 72. Accordingly, it is possible to prevent liquid drops of the reagent contained in the reagent container 90 from attaching to the antenna part 66 through the cutout part 72, and to prevent the reagent container 90 from being brought into contact with the antenna part 66 through the cutout part 72 when the reagent container 90 is to be set. Further, since the protection member 67 can also be used as an attachment member for the antenna part 66, the number of components can be reduced compared with a case where the antenna part 66 and the protection member 67 are separately attached to the holder part 60.

In the present embodiment, as described above, each of the five holder parts 60 (60a to 60e) includes the left face part 70 and the right face part 80 being the radio wave blocking part. Further, the antenna part 66 and the right face part 80 of each holder part 60 are arranged so as to face each other relative to the RFID tag 91 when the reagent container 90 is set in the setting part 62. In this configuration, by providing the left face part 70 and the right face part 80 to each holder part 60, it is possible to make a unit in which the antenna part 66, the setting part 62, and the left face part 70 and the right face part 80 as the radio wave blocking part are provided in the holder part 60. Accordingly, compared with a case where each holder part 60, and the left face part 70 and the right face part 80 (the radio wave blocking part) are separately provided, it is possible to simplify the apparatus configuration in which a plurality of holder parts 60 are provided.

In the present embodiment, as described above, the five holder parts 60a to 60e are arranged side by side in the predetermined direction (X direction). In addition, in each of the five holder parts 60a to 60e, the antenna part 66, the setting part 62, and the right face part 80 are arranged in this order from left (X1 direction side) along the predetermined direction. In this configuration, in each of the plurality of holder parts 60a to 60e arranged side by side along the X direction, a right face part 80 is always arranged between the antenna part 66 of one of two adjacent holder parts 60 and the setting part 62 of the other of the two adjacent holder parts 60. Accordingly, also in a case where the five holder parts 60a to 60e are arranged close to each other in the X direction, it is possible to assuredly perform reading/writing of information from/to the RFID tag 91 (91a to 91e) of the target reagent container 90 (each reagent container 90a to 90e set in its corresponding holder part 60a to 60e), while blocking the communication paths to the RFID tags 91 of the reagent containers 90 set in the setting parts 62 of other holder parts 60.

In the present embodiment, as described above, each holder part 60 includes the guide parts 71 and 81 which guide the reagent container 90 such that the RFID tag 91 of the reagent container 90 set in the setting part 62 is located so as to face its corresponding antenna part 66. In this configuration, since the RFID tag 91 and the antenna part 66 can be located so as to face each other by means of the guide parts 71 and 81, it is possible to more assuredly perform radio wave communication between the RFID tag 91 of the target reagent container 90 and the antenna part 66.

In the present embodiment, as described above, the guide parts 71 and 81 also serve as the radio wave blocking part. In this configuration, since the guide parts 71 and 81 which guide the reagent container 90 can function as the radio wave blocking part themselves, the number of components can be reduced compared with a case where the guide parts 71 and 81 and the radio wave blocking part are separately provided.

In the present embodiment, as described above, the left face part 70 (the guide part 71) and the right face part 80 (the guide part 81) are made of metal. In this configuration, radio waves from antenna parts 66 can be reflected at the left face part 70 (the guide part 71) and the right face part 80 (the guide part 81) which are made of metal. Thus, it is possible to easily prevent occurrence of erroneous reading/writing of information from/to the RFID tags 91 of reagent containers 90 other than the target reagent container 90.

In the present embodiment, as described above, the chassis 61 including the left face part 70 and the right face part 80 is grounded. In this configuration, it is possible to suppress the left face part 70 and the right face part 80 (the chassis 61) themselves which are made of metal, from becoming a noise source. Thus, a good radio wave blocking effect can be obtained.

(First Modification)

In the above embodiment, an example has been shown in which the antenna parts 66 of the respective holder parts 60 (60a to 60e) and the RFID tags 91 of the reagent containers 90 set in the respective holder parts 60 (60a to 60e) are linearly arranged in the X direction. However, as in a first modification shown in FIG. 11, the antenna parts of the respective holder parts and the RFID tags may not be linearly arranged in the X direction.

Figure 11:
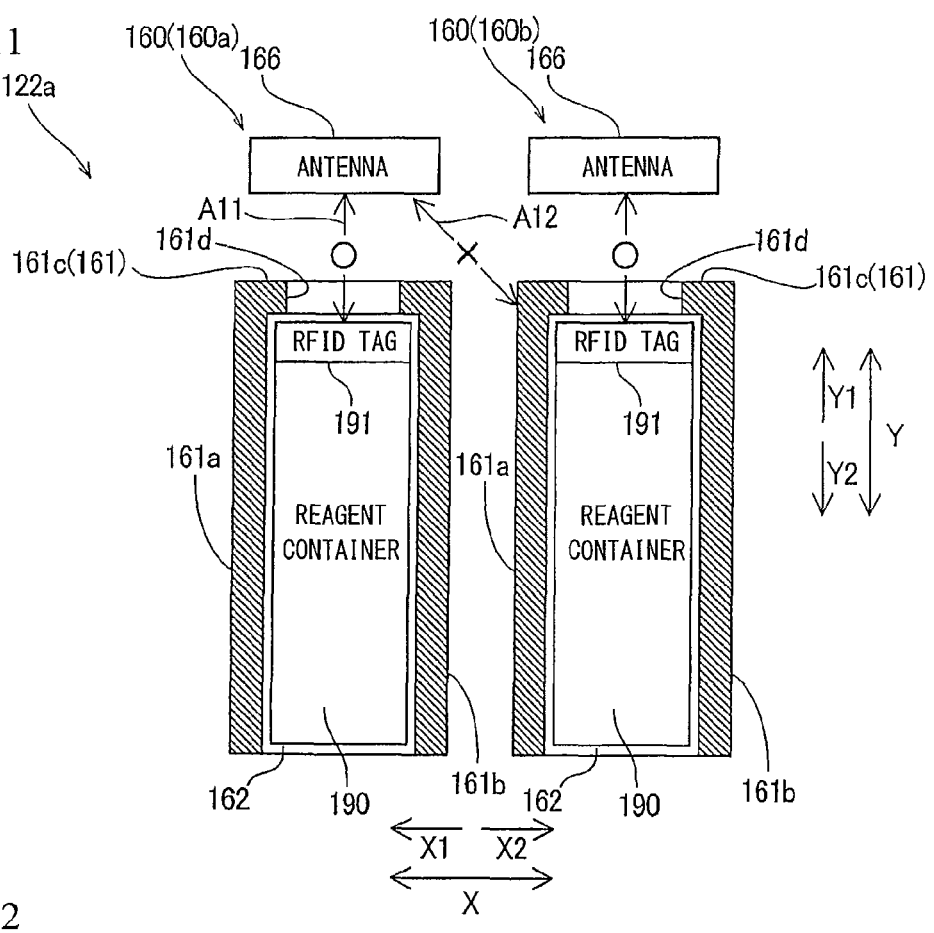
FIG. 11 is a schematic diagram showing a first modification of a reagent storage section of the second measurement unit according to an embodiment of the present invention.

As shown in FIG. 11, in a reagent storage section 122a according to the first modification of the present embodiment, an antenna part 166 of each holder part 160 (160a and 160b) is arranged to the depth side (Y1 direction side) of a setting part 162. Moreover, an RFID tag 191 is attached to a front face (leading portion) of each reagent container 190. It is configured such that the antenna part 166 faces the RFID tag 191 of the reagent container 190 set in the setting part 162 face each other in a front-rear direction (Y direction).

The chassis 161 of the holder part 160 (160a and 160b) includes a left face part 161a, a right face part 161b, and a depth side part 161c, and is provided so as to surround the setting part 162 (the reagent container 190) except a rear portion (Y1 direction side) of the setting part 162. In the depth side part 161c on the depth side (Y1 direction side) of the setting part 162, a cutout part 161d is formed.

Thus, the antenna part 166 of the holder part 160a on the X1 direction side can communicate with the RFID tag 191 of the reagent container 190 set in the holder part 160a, through a communication path A11 in the Y direction via the cutout part 161d. On the other hand, between the RFID tag 191 of the reagent container 190 in the holder part 160b adjacent to the holder part 160a in the X2 direction and the antenna part 166 of the holder part 160a, the left face part 161a and the depth side part 161c as a radio wave blocking part of the holder part 160b are arranged. Therefore, a communication path A12 between the antenna part 166 of the holder part 160a and the RFID tag 191 of the reagent container 190 in the adjacent holder part 160b is blocked by the left face part 161a and the depth side part 161c of the holder part 160b. The same similarly applies to the antenna part 166 of the holder part 160b, and thus, description thereof is omitted.

As described above, even in the case where the antenna part 166 and the RFID tag 191 of the reagent container 190 set in the setting part 162 face each other in the front-rear direction (Y direction) as in the holder part 160 (160a and 160b) of the first modification, similar effects to those of the above embodiment can be obtained.

(Second Modification)

In the above embodiment, an example has been shown in which the antenna parts 66 of the respective holder parts 60a to 60e and the RFID tags 91 of the reagent containers 90 held therein are alternately arranged in the X direction. However, as shown in the second modification shown in FIG. 12, the antenna parts and the RFID tags may not be arranged alternately.

Figure 12:
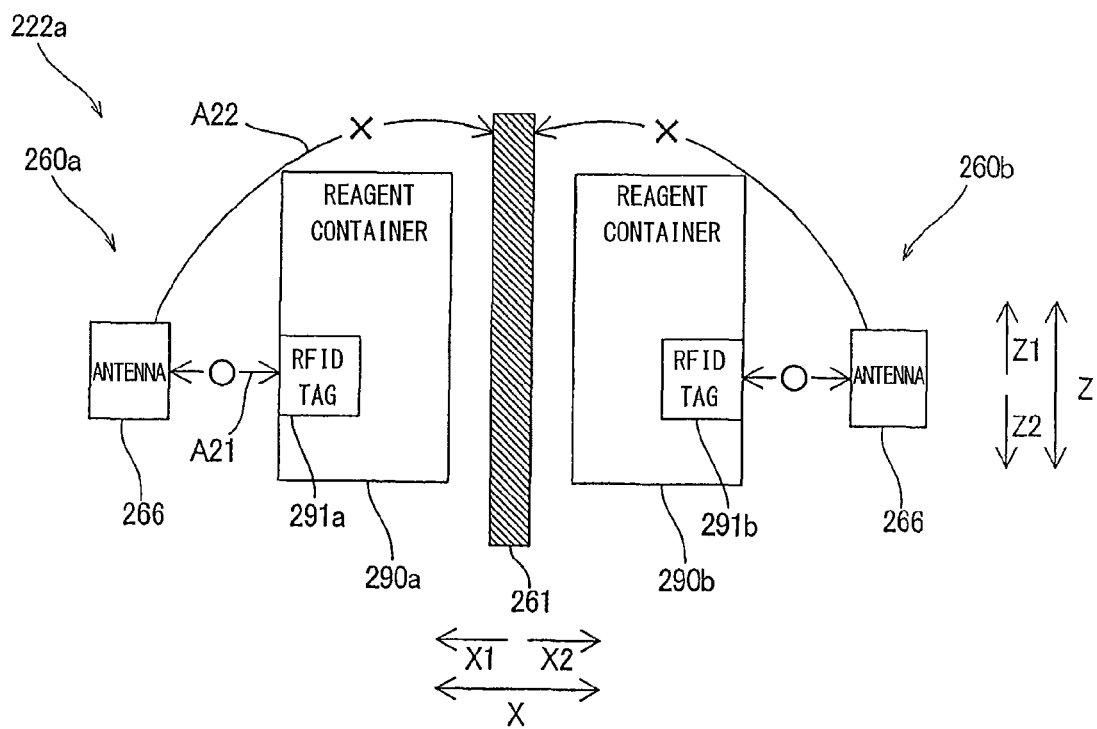
FIG. 12 is a schematic diagram showing a second modification of the reagent storage section of the second measurement unit according to an embodiment of the present invention.

As shown in FIG. 12, in a reagent storage section 222a according to the second modification of the present embodiment, a holder part 260a and a holder part 260b are arranged in line symmetry relative to a radio wave blocking part 261. The radio wave blocking part 261 is formed of a metallic separation plate which separates the holder part 260a from the holder part 260b. The radio wave blocking part 261 is provided so as to extend in the up-down direction (Z direction) and the depth direction.

In the reagent storage section 222a, the holder part 260a is arranged to the X1 direction side and the holder part 260b is arranged to the X2 direction side, relative to the radio wave blocking part 261. In the holder part 260a and the holder part 260b, reagent containers 290a and 290b are arranged to the side of the radio wave blocking part 261 arranged in the center, and antenna parts 266 are arranged outside the reagent containers 290a and 290b, respectively. Accordingly, in the second modification, the reagent container 290a set in the holder part 260a has an RFID tag 291a attached to its side face on the X1 direction side where its corresponding antenna part 266 is arranged. Moreover, the reagent container 290b set in the holder part 260b has an RFID tag 291b attached to its side face on the X2 direction side where its corresponding antenna part 266 is arranged.

In the second modification, the antenna part 266 of the holder part 260a can communicate with the RFID tag 291a of the reagent container 290a set in the holder part 260a, through a communication path A21 in the X direction. On the other hand, since the radio wave blocking part 261 is provided between the holder part 260a and the holder part 260b, a communication path A22 between the antenna part 266 of the holder part 260a and the RFID tag 291b of the reagent container 290b in the adjacent holder part 260b is blocked by the radio wave blocking part 261. The same similarly applies to the antenna part 266 of the holder part 260b, and thus description thereof is omitted.

(Third Modification)

In the above embodiment, an example has been shown in which the holder parts 60a to 60e are arranged side by side in the X direction. However, as in a third modification shown in FIG. 13, the holder parts may be arranged in the up-down direction.

Figure 13:
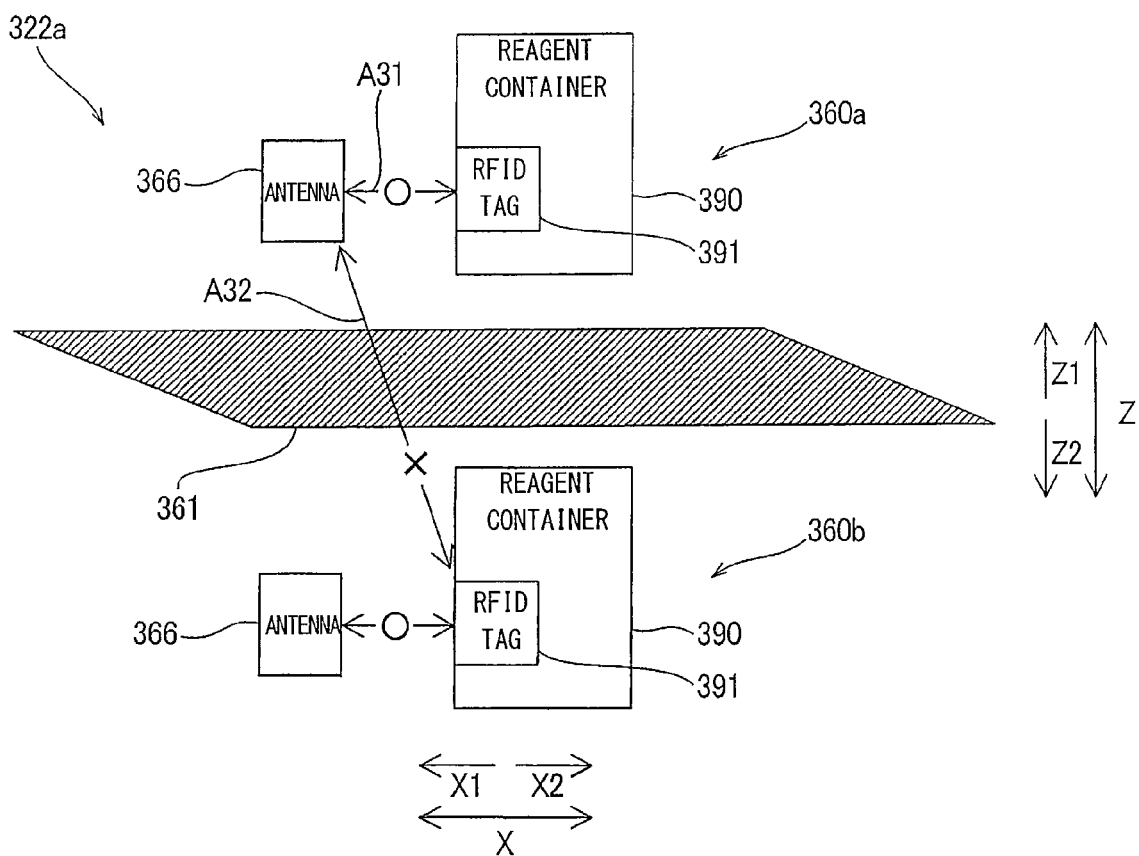
FIG. 13 is a schematic diagram showing a third modification of the reagent storage section of the second measurement unit according to an embodiment of the present invention.

As shown in FIG. 13, in a reagent storage section 322a according to the third modification of the present embodiment, a holder part 360a on the upper side (Z1 direction side) and a holder part 360b on the lower side (Z2 direction side) are arranged in a line in the up-down direction relative to a radio wave blocking part 361.

Each of the holder parts 360a and 360b is configured such that an antenna part 366 is located on the X1 direction side and a reagent container 390 is set on the X2 direction side. Accordingly, each of the holder parts 360a and 360b is configured such that the antenna part 366 and an RFID tag 391 of the reagent container 390 face each other in the X direction. The radio wave blocking part 361 is provided so as to extend in the horizontal direction (X direction and depth direction). Therefore, the antenna part 366 and the reagent container 390 (the RFID tag 391) in the holder part 360a, and the antenna part 366 and the reagent container 390 (the RFID tag 391) in the holder part 360b are respectively arranged in the up-down direction, relative to the radio wave blocking part 361.

In the third modification, the antenna part 366 of the holder part 360a can communicate with the RFID tag 391 of the reagent container 390 set in the holder part 360a, through a communication path A31 in the X direction. On the other hand, since the radio wave blocking part 361 is provided between the holder part 360a and the holder part 360b, a communication path A32 between the antenna part 366 of the holder part 360a and the RFID tag 391 of the reagent container 390 in the holder part 360b, which is on the lower side and adjacent to the holder part 360a, is blocked by the radio wave blocking part 361. The same similarly applies to the antenna part 366 of the holder part 360b, and thus, description thereof is omitted.

(Fourth Modification)

In the above embodiment, an example has been shown in which the reagent containers 90 each having the same shape can be set in the five holder parts 60 (60a to 60e), respectively. However, as in a fourth modification shown in FIG. 14, reagent containers having different sizes may be set in the holder parts, respectively.

Figure 14:
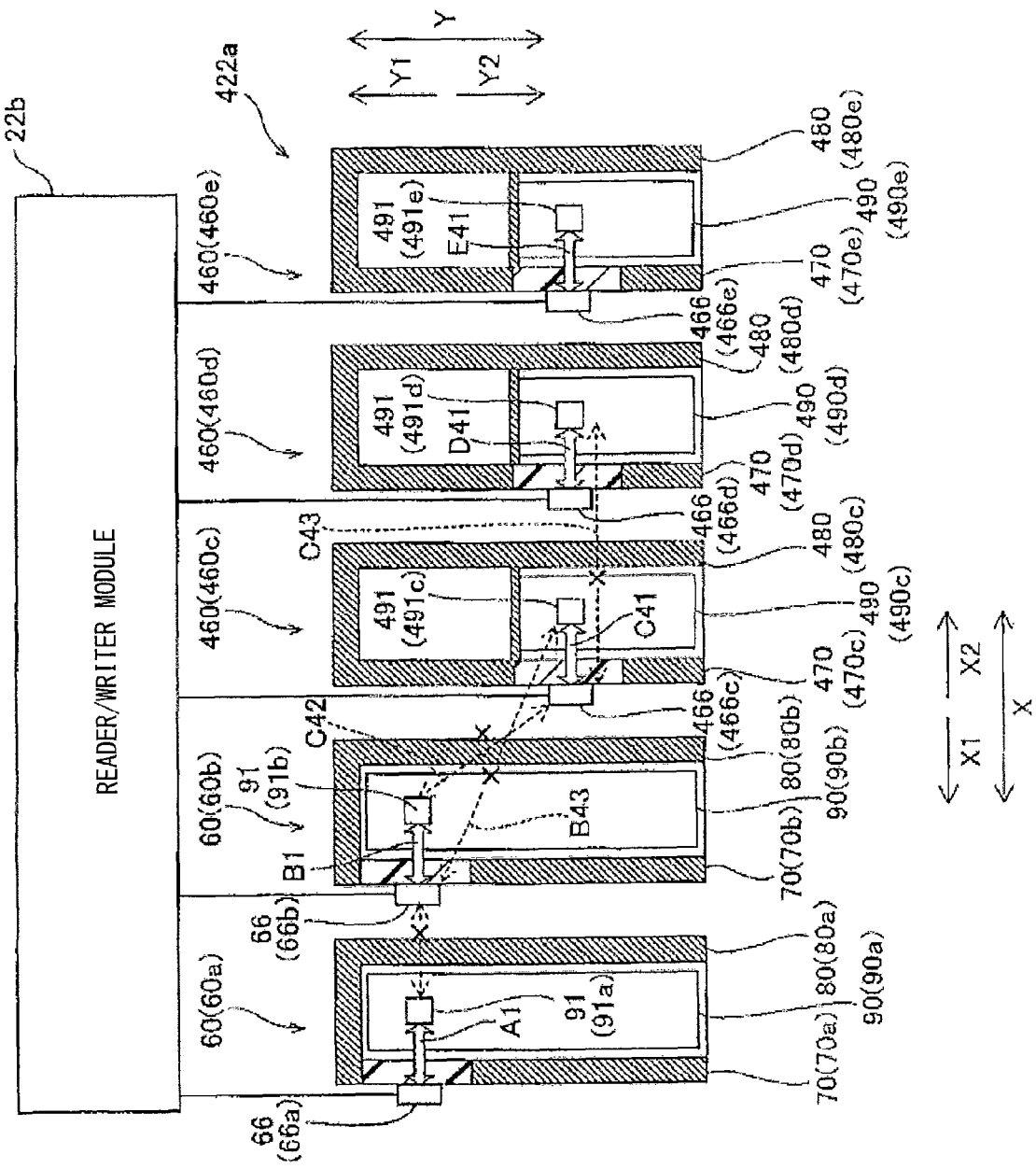
FIG. 14 is a schematic diagram showing a fourth modification of the reagent storage section of the second measurement unit according to an embodiment of the present invention.

As shown in FIG. 14, in a reagent storage section 422a according to the fourth modification of the present embodiment, two holder parts 60 (60a and 60b) capable of having set therein the large reagent containers 90 (90a and 90b) and three holder parts 460 (460c to 460e) capable of having set therein small reagent containers 490 (490c to 490e) are arranged side by side in the X direction. It should be noted that the structures of each holder part 60 and each reagent container 90 are the same as those in the above embodiment. Each reagent container 490 is configured to have a length in the longitudinal direction (Y direction) shorter than that of the reagent container 90, and is configured to contain a smaller amount of a reagent than that of the reagent container 90.

Each holder part 460 includes a left face part 470 (470c to 470e) and a right face part 480 (480c to 480e). Since the small reagent container 490 is set in the holder part 460, an antenna part 466 (466c to 466e) is located at a position facing an RFID tag 491 (491c to 491e) in the X direction, in a front portion (Y2 direction side) of the holder part 460. Accordingly, the position of the cutout part in the left face part 470 of the holder part 460 is also shifted to the Y2 direction side. In this manner, the antenna part 66 of each holder part 60 and the antenna part 466 of each holder part 460 are arranged at positions shifted from each other in the Y direction.

Here, when focusing on the holder part 60b, the antenna part 66b of the holder part 60b can communicate with the RFID tag 91b of the reagent container 90b set in the holder part 60b, through a communication path B1. On the other hand, a communication path B43 between the RFID tag 491c of the reagent container 490c set in the holder part 460c adjacent to the holder part 60b in the X2 direction and the antenna part 66b of the holder part 60b is blocked (radio waves are reflected) by the right face part 80b of the holder part 60b.

When focusing on the holder part 460c, the antenna part 466c of the holder part 460c can communicate with the RFID tag 491c of the reagent container 490c set in the holder part 460c, through a communication path C41. On the other hand, a communication path C42 between the RFID tag 91b of the reagent container 90b set in the holder part 60b adjacent to the holder part 460c in the X1 direction and the antenna part 466c of the holder part 460c is blocked (radio waves are reflected) by the right face part 80b of the holder part 60b. Moreover, a communication path C43 between the RFID tag 491d of the reagent container 490d set in the holder part 460d adjacent to the holder part 460c in the X2 direction and the antenna part 466c of the holder part 460c is blocked (radio waves are reflected) by the right face part 480c of the holder part 460c.

As a result, the antenna parts 66a, 66b, and 466c to 466e of the holder parts 60a, 60b, and 460c to 460e can communicate with the RFID tags 91a, 91b, and 491c to 491e of their corresponding reagent containers 90a, 90b and 490c to 490e, only through their corresponding communication paths A1, B1, and C41 to E41.

It should be noted that the embodiment and the first to fourth modifications disclosed herein are merely illustrative in all aspects and should not be considered as being restrictive. The scope of the present invention is defined by the scope of the claims not by the description of the embodiment and the first to fourth modifications described above, and includes meaning equivalent to the scope of the claims and all modifications within the scope.

For example, in the above embodiment, as an example of an analyzer, an example has been shown in which two measurement units, i.e., the first measurement unit and the second measurement unit, are provided. However, the present invention is not limited thereto. One, or three or more measurement units may be provided.

Further, in the above embodiment, a blood analysis system that includes two measurement units, a sample transporting apparatus, and a control device has been shown. However, the present invention is not limited thereto. The present invention may be applied to a single measurement unit, without forming the analysis system as described above.

In the above embodiment and the fourth modification, examples have been shown in which five holder parts are provided in the reagent storage section. In the first to third modifications, examples have been shown in which two holder parts are provided in the reagent storage section. However, the present invention is not limited thereto. Three or four holder parts may be provided, or alternatively, six or more holder parts may be provided. The holder parts may be provided by the number corresponding to the types of reagents used in the analyzer.

Further, in the above embodiment, an example has been shown in which the left face part and the right face part as the radio wave blocking part are made of metal. However, the present invention is not limited thereto. As long as being able to block radio waves, the radio wave blocking part may be made of a resin material other than metal.

The radio wave blocking part made of metal blocks radio waves by reflecting them. However, the radio wave blocking part may not reflect radio waves. Therefore, as the radio wave blocking part, a radio wave absorbing material (ferrite sheet) which absorbs radio waves may be provided, for example. With respect to the radio wave blocking part of the present invention, it is sufficient that it can substantially block radio waves, and the radio wave blocking part includes those that attenuate radio waves without completely blocking radio waves. That is, it is sufficient that the radio wave blocking part is configured to attenuate radio waves to an extent that does not allow the antenna part of one holder part to communicate with the RFID tags of reagent containers set in other holder parts.

In the above embodiment, an example has been shown in which guide parts are integrally provided in the left face part and the right face part as the radio wave blocking part, and the guide parts also serve as the radio wave blocking part. However, the present invention is not limited thereto. In the present invention, the guide parts may be provided separately from the left face part and the right face part, or the guide parts may not be provided. Further, the guide parts may not serve also as the radio wave blocking part.

In the above embodiment, an example has been shown in which a cutout part as the radio wave transmissive part is provided in the left face part. However, the present invention is not limited thereto. For example, in a part of the left face part as the radio wave blocking part, there may be provided a radio wave transmissive part made of a radio wave transmissive material that allows radio waves to pass therethrough.

In the above embodiment, an example has been shown in which the protection member is formed from a resin material (polyacetal) which allows radio wave communication to pass therethrough. However, the present invention is not limited thereto. In the present invention, the protection member may be formed from a resin material other than polyacetal, or may be formed from a radio wave transmissive material other than a resin material.

What is claimed is:

1. A sample analyzer which analyzes a sample using a reagent contained in a reagent container, the sample analyzer comprising:
    at least one measurement unit configured to measure the sample;
    a reagent storage section including a plurality of reagent holder parts, each of the reagent holder parts including;
        a setting part supporting a reagent container having a storage medium attached thereto, and
        a chassis having a set of face parts upstanding from the setting part, each face part separated by a space from the face parts of adjacent reagent holder parts,
    wherein a cutout resides at a predetermined position on one of the face parts and a protection member resides on the one face part and covers the cut out, and
    wherein the setting part includes a spring member and a shaft, the setting part is configured to rotate about the shaft under a force applied by the spring member to bring an opening of the reagent container into alignment with an aspiration tube;
    a plurality of radio wave communication parts, each positioned on each protection member, so as to transmit and receive a radio wave to and from the storage medium of the reagent container through the protection member; and
    wherein the face parts comprise a conductive material to block radio wave communication paths between the radio wave communication part of each of the reagent holder parts and the storage mediums of the reagent containers in the adjacent reagent holder parts.

2. The sample analyzer of claim 1, wherein the face parts are between the radio wave communication parts of the reagent holder parts and the storage medium of the reagent container in the adjacent reagent holder parts.

3. The sample analyzer of claim 1, wherein each of the reagent holder parts comprises a shape surrounding the reagent container in the setting part thereof.

4. The sample analyzer of claim 3, wherein the conductive material includes the cutout at a position corresponding to the radio wave communication part.

5. The sample analyzer of claim 4, wherein the cutout comprises a shape other than a loop.

6. The sample analyzer of claim 4, wherein the protection member covering the cutout comprises a radio wave transmissive material that allows a radio wave to pass therethrough, wherein the radio wave communication parts are attached to respective protection members.

7. The sample analyzer of claim 1, wherein the plurality of reagent holder parts reside in a line along a predetermined direction, and each of the reagent holder parts includes the radio wave communication part thereof, the setting part thereof, and the face part thereof along the predetermined direction in this order.

8. The sample analyzer of claim 1, wherein each reagent holder part comprises a guide part which guides the reagent container such that the storage medium of the reagent container is located so as to face the radio wave communication part corresponding thereto.

9. The sample analyzer of claim 1, wherein the face parts comprise a metal.

10. The sample analyzer of claim 9, wherein the face parts are grounded.

11. The sample analyzer of claim 1, wherein the plurality of reagent holder parts comprises three or more reagent holder parts.

12. The sample analyzer of claim 11, wherein the plurality of reagent holder parts reside side by side in a line along a horizontal direction.

13. The sample analyzer of claim 1, wherein each radio wave communication part reads reagent-relating-information stored in the storage medium corresponding thereto and writes information into the storage medium, by transmitting and receiving a radio wave.

14. The sample analyzer of claim 13, wherein the reagent-relating-information includes at least one of a type, a lot number, and an expiration date of a reagent.

15. The sample analyzer of claim 1, wherein the sample comprises blood, and the sample analyzer comprises a blood analyzer that analyzes components in blood using the reagent in the reagent container.

16. The sample analyzer of claim 15, wherein the blood comprises whole blood, and the sample analyzer comprises a blood cell counter that stains blood cells included in the whole blood using staining reagent in the reagent container and counts the stained blood cells.

17. The sample analyzer of claim 1, wherein each setting part includes the aspiration tube and the aspiration tube accesses the reagent in the reagent container from above through the opening located in an upper face of the reagent container, each storage medium resides on a side face of a reagent container, and each radio wave communication part is in close proximity to the storage medium of the reagent container.

18. The sample analyzer of claim 17, wherein the setting part includes a cover movable in an up-down direction and that opens and closes a reagent container inlet, and the aspiration tube is configured to enter the reagent container, associated with a movement of the cover being closed.

19. The sample analyzer of claim 1, wherein each setting part is configured to hold a reagent container, such that a bottom surface of the reagent container is inclined, and each setting part includes an aspiration tube inserted into the reagent container, such that a tip of the aspiration tube is located at a lower level side of the inclined bottom surface.

* * * * *